United States Patent [19]

Martin et al.

[11] Patent Number: 4,742,061
[45] Date of Patent: * May 3, 1988

[54] BENZO C[C]-1,5-NAPHTHYRIDINES AND RELATED COMPOUNDS AS MEMORY ENHANCING AGENTS

[75] Inventors: Lawrence L. Martin, Lebanon; Linda L. Setescak, Somerville; Susan J. Scott, No. Brunswick, all of N.J.

[73] Assignee: Hoechst-Roussel Pharmaceuticals Inc., Somerville, N.J.

[*] Notice: The portion of the term of this patent subsequent to Mar. 24, 2004 has been disclaimed.

[21] Appl. No.: 870,585

[22] Filed: Jun. 4, 1986

Related U.S. Application Data

[63] Continuation-in-part of Ser. No. 711,327, Mar. 13, 1985, Pat. No. 4,652,567.

[51] Int. Cl.$^4$ .................. A61K 31/495; A61K 31/435; C07D 401/14; C07D 487/04
[52] U.S. Cl. .................................... 514/254; 514/292; 544/361; 546/81
[58] Field of Search .......................... 544/361; 546/81; 514/253, 254, 292

[56] References Cited

FOREIGN PATENT DOCUMENTS 2273533 1/1976 France .

OTHER PUBLICATIONS

Bauer & Hewitson, J. Org. Chem. 27, 3982 (1962).
Thyagarjan, Mechanism of Molecular Migrations pp. 251-289 (1971).
Campaigne, Mathews, J. Heterocyclic Chem. 12, 391 (1975).
Kolocouris, Rigo, Chimika Chronika, New Series II, 309 (1982).
Rigo, Fossaet, de Ouilarg & Kolocouris, J. Heterocyclic Chem. 21, 1381 (1984).
Ferlux, CA 85-32835X.
Soman, Merck Index, 10th Edition, 8559.
Tabun, Merck Index, 10th Edition, 8904.
Peter Davies, Drug Development Research 5:69-76 (1985).
Summers et al., The New England Journal of Medicine vol. 315, No. 20, (1986) pp. 1241-1245.
Goodman and Gilman's The Pharmacological Basis of Therapeutics Sixth Edition (1980) Chapter 6, Anticholinesterase Agent.
Johns et al., Drug Development Research 5:77-96 (1985).
Schindler et al., Drug Development Research 4:567-576 (1984).
Bartus et al., Science vol. 209 (1980) pp. 301-303.
Coyle et al., Science 219, 1184-1190 (1983).
Davis et al., The New England Journal of Medicine vol. 315, No. 2 (1986) pp. 1286-1287.

Primary Examiner—Donald G. Daus
Assistant Examiner—Cecilia Shen
Attorney, Agent, or Firm—Tatsuya Ikeda

[57] ABSTRACT

There are disclosed novel compounds of the formula

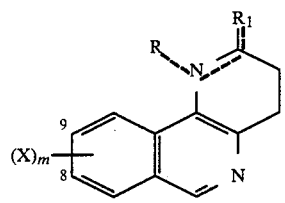

where m is 1 or 2; each X is independently H, halogen, loweralkyl, loweralkoxy, —$CF_3$, or —OH; R is H, loweralkyl, chloroloweralkyl, bromoloweralkyl, iodoloweralkyl, aminoloweralkyl, loweralkylaminoloweralkyl, diloweralkylaminoloweralkyl, arylloweralkyl, diarylloweralkyl, thienylloweralkyl, furylloweralkyl, loweralkanoyl, chloroloweralkanoyl, bromoloweralkanoyl, iodoloweralkanoyl, aminoloweralkanoyl, loweralkylaminoloweralkanoyl, diloweralkylaminoloweralkanoyl, aroyl, arylloweralkanoyl or diarylloweralkanoyl, thienylloweralkanoyl, furylloweralkanoyl; and $R_1$ is =O,

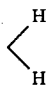

or —$NR_2R_3$, $R_2$ and $R_3$ being independently H or loweralkyl, or taken together with the nitrogen atom to which they are attached constituting

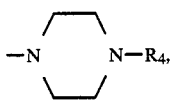

$R_4$ in turn being H, loweralkyl, hydroxyloweralkyl, aryl, arylloweralkyl or diarylloweralkyl, with the proviso that when $R_1$ is —$NR_2R_3$, R is nonexistent, that when $R_1$ is =O, R is not an acyl group and that when $R_1$ is

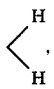

R is not chloroloweralkyl, bromoloweralkyl or iodoloweralkyl; or pharmaceutically acceptable acid addition salts thereof, which are useful for enhancing memory.

105 Claims, No Drawings

BENZO[C]-1,5-NAPHTHYRIDINES AND RELATED COMPOUNDS AS MEMORY ENHANCING AGENTS

This is a continuation-in-part of U.S. Ser. No. 711,327, filed Mar. 13, 1985, now U.S. Pat. No. 4,652,567.

This invention relates to novel compounds of the formula

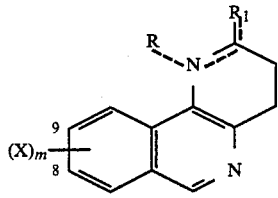

where m is 1 or 2; each X is independently H, halogen, loweralkyl, loweralkoxy, —$CF_3$, or —OH; R is H, loweralkyl, chloroloweralkyl, bromoloweralkyl, iodoloweralkyl, aminoloweralkyl, loweralkylaminoloweralkyl, diloweralkylaminoloweralkyl, arylloweralkyl, diarylloweralkyl, thienylloweralkyl, furylloweralkyl, loweralkanoyl, chloroloweralkanoyl, bromoloweralkanoyl, iodoloweralkanoyl, aminoloweralkanoyl, loweralkylaminoloweralkanoyl, diloweralkylaminoloweralkanoyl, aroyl, arylloweralkanoyl or diarylloweralkanoyl, thienylloweralkanoyl, furylloweralkanoyl; and $R_1$ is =O,

or —$NR_2R_3$, $R_2$ and $R_3$ being independently H or loweralkyl, or taken together with the nitrogen atom to which they are attached constituting

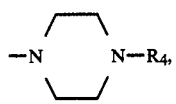

$R_4$ in turn being H, loweralkyl, hydroxyloweralkyl, aryl, arylloweralkyl or diarylloweralkyl, with the proviso that when $R_1$ is —$NR_2R_3$, R is nonexistent, that when $R_1$ is =O, R is not an acyl group and that when $R_1$ is

R is not chloroloweralkyl, bromoloweralkyl or iodoloweralkyl; or pharmaceutically acceptable acid addition salts thereof, which are useful for enhancing memory, methods for synthesizing them, pharmaceutical compositions comprising an effective memory enhancing amount of such a compound and methods of treating a patient in need of memory enhancement by administering such a compound to the patient.

This invention also relates to novel compounds of the formula

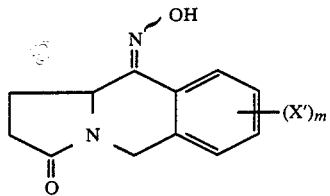

where m is 1 or 2 and each X' is independently H, halogen, loweralkyl, loweralkoxy or $CF_3$, which are useful as an intermediate for synthesizing compounds I.

Throughout the specification and the appended claims, a given chemical formula or name shall encompass all stereo, optical, and geometrical isomers thereof where such isomers exist, as well as pharmaceutically acceptable acid addition salts thereof and solvates thereof such as for instance hydrates.

The following general rules of terminology shall apply throughout the specification and the appended claims.

Unless otherwise stated or indicated, the term loweralkyl denotes a straight or branched alkyl group having from 1 to 6 carbon atoms. Examples of said loweralkyl group include methyl, ethyl, n-propyl, iso-propyl, n-butyl, iso-butyl, sec-butyl, t-butyl and straight- and branched-chain pentyl and hexyl.

Unless otherwise stated or indicated, the term loweralkoxy denotes a straight or branched alkoxy group having from 1 to 6 carbon atoms. Examples of said loweralkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term halogen shall mean fluorine, chlorine, bromine or iodine.

Unless otherwise stated or indicated, the term aryl shall mean a phenyl group having 0, 1, 2 or 3 substituents each of which being independently loweralkyl, loweralkoxy, halogen or $CF_3$, and the term diaryl shall mean two such aryl groups each of which being independent of the other.

The term loweralkanoyl shall mean a group obtained by removing a hydroxy group from the carboxyl group of a loweralkanoic acid, and thus it includes for instance formyl, acetyl and the like.

The term aroyl shall mean arylcarbonyl, the term aryl having the meaning as defined above.

The term arylloweralkanoyl shall mean a loweralkanoyl group having an aryl substituent thereon, the terms loweralkanoyl and aryl having the respective meanings defined above.

The compounds of this invention are prepared by following one or more of the steps described below. Throughout the description of the synthetic steps, the definitions of m, X, X', R and $R_1$ through $R_4$ are as given above unless otherwise stated or indicated, and $R_5$ appearing below shall mean loweralkyl, chloroloweralkyl, bromoloweralkyl, iodoloweralkyl, arylloweralkyl, diarylloweralkyl, thienylloweralkyl or furylloweralkyl, $R_6$ appearing below shall mean H, loweralkyl, chloroloweralkyl, bromoloweralkyl, iodoloweralkyl, aryl, arylloweralkyl, diarylloweralkyl, thienylloweralkyl or furylloweralkyl, and $R_7$ appearing below shall mean H, loweralkyl, aminoloweralkyl, loweralkylaminoloweralkyl, diloweralkylaminoloweralkyl, aryl, arylloweralkyl, diarylloweralkyl, thienylloweralkyl or furylloweralkyl.

STEP A

The compound of formula III below is cyclized to afford compound of formula IV below.

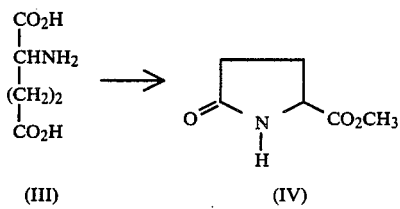

Said cyclization is typically conducted by refluxing an aqueous solution of compound III, followed by isolation and esterification with acidic methanol.

STEP B

Compound IV is reacted with a compound of formula V below in the presence of a strong base such as NaH to afford a compound of formula VI below.

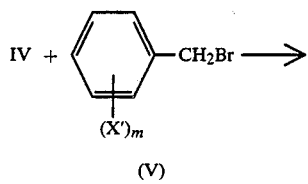

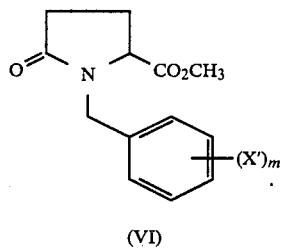

Said reaction is conveniently conducted in a suitable solvent such as an anhydrous aromatic compound, namely, toluene or the like at a temperature of about 80°–100° C.

STEP C

Compound VI is hydrolyzed to afford a compound of formula VII below.

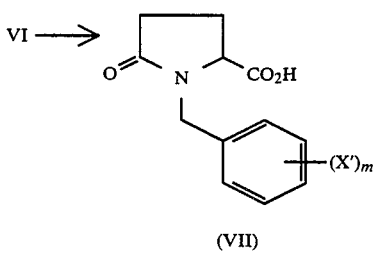

Said hydrolysis is conveniently conducted in an aqueous system containing compound VI and an alkaline substance such as sodium hydroxide and heating the system with a steam bath.

STEP D

The carboxyl group of compound VII is converted to its acid chloride with a suitable agent such as thionyl chloride and the resultant acid chloride compound is cyclized under a Friedel-Crafts condition to afford a compound of the formula VIII below.

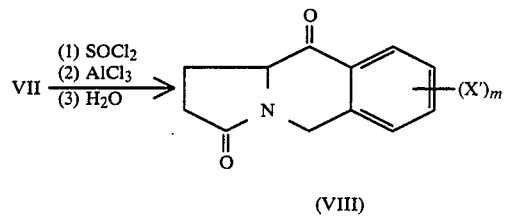

Said reaction is typically conducted by dissolving compound VII and thionyl chloride in a suitable solvent such as dichloromethane and refluxing the solution. The Friedel-Crafts reaction is typically conducted by adding $AlCl_3$ to the solution remaining after the acid chloride formation step and stirring the resultant mixture at or below the ambient temperature.

STEP E

Compound VIII is reacted with hydroxylamine to afford the aforementioned compound II.

Said oxime formation reaction is conveniently conducted, for instance, by preparing a suspension comprising compound VIII, hydroxylamine hydrochloride, water, ethanol and a weak base such as sodium acetate and refluxing the suspension.

STEP F

The oxime compound of the formula II is converted to a compound of the formula Ia below by heating it in a substantially anhydrous acidic medium.

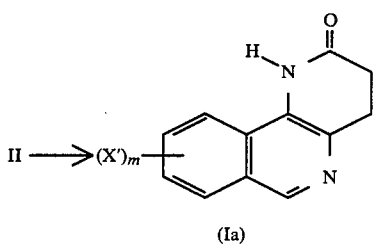

It is convenient to conduct the above reaction by adding compound II to a vigorously stirred large excess of polyphosphoric acid at a temperature of about 100°–150° C., but since this reaction may be considered a species of so-called Wolff-Semmler aromatization reaction (see for instance "Mechanisms of Molecular Migrations", Volume 4, edited by B. S. Thyagarajan, Wiley-Interscience, New York, 1971), other suitable reaction conditions used for Wolff-Semmler aromatization reactions may also be used to effect the above reaction step, including the use of so-called Beckmann's mixture which is a mixture of hydrogen chloride, acetic acid and acetic anhydride.

STEP G

After compounds Ia have been obtained, the corresponding compounds having one or two hydroxy groups on the benzene ring can be prepared by subjecting compounds Ia where one or both of the group X' are methoxy to a cleavage reaction. Typically, this cleavage reaction can be accomplished by reacting the methoxy compounds with pyridine hydrochloride at a temperature of about 200°–220° C.

By virtue of this step and STEP F, compounds of formula Ib below are obtained.

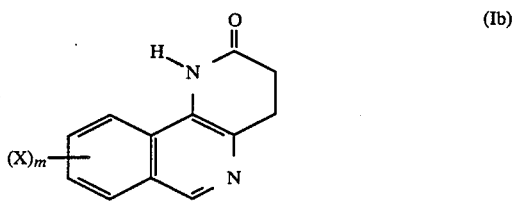

(Ib)

STEP H

Compound Ib is reacted with an amine of the formula NHR$_2$R$_3$ to afford a compound of the formula Ic below.

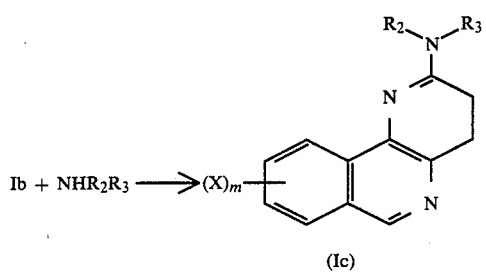

(Ic)

Said reaction is typically conducted in the presence of TiCl$_4$ and a suitable solvent such as anhydrous tetrahydrofuran at a temperature of about 0°–40° C.

STEP I

Compound Ib is reacted with a compound of the formula R$_5$-Hal where R$_5$ is as defined earlier and Hal is bromine, chlorine or iodine to afford a compound of the formula Id below.

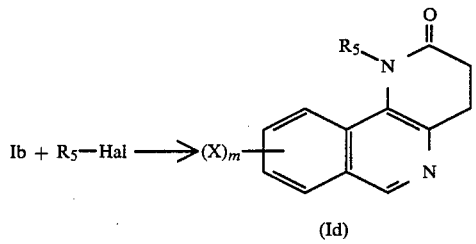

(Id)

Said reaction is conducted typically in the presence of an acid scavenger such as KOH or the like in a suitable solvent such as dimethylsulfoxide at a temperature of about 20°–50° C.

When the group R$_5$ in formula Id is chloroloweralkyl, bromoloweralkyl or iodoloweralkyl, namely, when the group R$_5$ contains a chlorine, bromine or iodine atom in addition to the "Hal", the leaving atom "Hal" in the above reaction should be chosen such that its reactivity is not substantially lower than that of the other halogen atom attached to R$_5$.

STEP J

When the group R$_5$ in compound Id is chloroloweralkyl, bromoloweralkyl or iodoloweralkyl, it can be converted to the corresponding aminoloweralkyl, loweralkylaminoloweralkyl or diloweralkylaminoloweralkyl by reacting compound Id with ammonia, loweralkylamine or diloweralkylamine, respectively, in a manner well known to the art.

STEP K

Compound Ib is reduced to afford a compound of the formula Ie below.

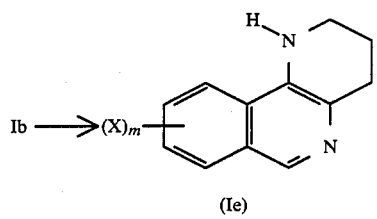

(Ie)

Said reduction is conducted for instance by reacting compound Ib with diborane in a suitable solvent such as anhydrous tetrahydrofuran at the ambient temperature or in the vicinity thereof.

STEP L

Compound Ie is reacted with a compound of the formula R$_6$COCl, where R$_6$ is as defined earlier except that it is not hydrogen, to afford a compound of formula If below.

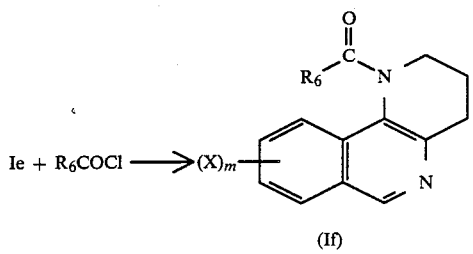

(If)

(R$_6 \neq$ H)

Said reaction is conveniently conducted in the presence of a suitable solvent such as pyridine and an excess of the acid chloride at a temperature of 20°–50° C.

When R$_6$ is hydrogen, compound If is prepared by reacting compound Ie with formic-acetic anhydride. Typically, the reaction is conducted by first preparing formic-acetic anhydride from acetic anhydride and concentrated formic acid (95–99% for instance) at about 40°–60° C. and then adding compound Id to the resultant solution and heating the reaction mixture at about 80°–100° C.

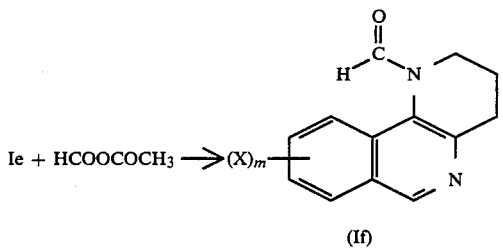

STEP M

When the group $R_6$ in compound If is chloroloweralkyl, bromoloweralkyl or iodoloweralkyl, it can be converted to the corresponding aminoloweralkyl, loweralkylaminoloweralkyl or diloweralkylaminoloweralkyl by reacting compound Ie with ammonia, loweralkylamine or diloweralkylamine, respectively, in a manner well known to the art.

STEP N

Compound If where $R_7$ is as defined earlier, is reduced to afford a compound of formula Ig below.

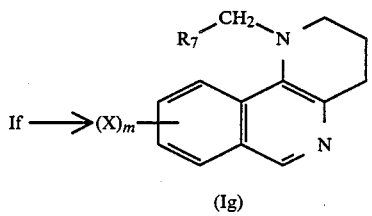

Said reduction is conducted for instance by reacting compound If with diborane in a suitable solvent such as anhydrous tetrahydrofuran at the ambient temperature or in the vicinity thereof.

The naphthyridine compounds of formula I of the present invention are useful in the treatment of various memory dysfunctions characterized by decreased cholinergic function, such as Alzheimer's disease. This utility is manifested by the ability of these compounds to inhibit the enzyme acetyl cholinesterase and thereby increase acetylcholine levels in the brain.

CHOLINESTERASE INHIBITION ASSAY

The ability to inhibit acetylcholinesterase was determined by the photometric method of Ellman et al., Biochem. Pharmacol. 7, 88 (1961).

| Compound | Cholinesterase Inhibition $IC_{50}$ (molar) |
| --- | --- |
| 1,2,3,4-Tetrahydrobenzo[c]-1,5-naphthyridine | $6.1 \times 10^{-5}$ |
| 3,4-Dihydro-2-(4-methyl-1-piperazinyl)benzo[c]-1,5-naphthyridine hemihydrate | $8.4 \times 10^{-4}$ |
| 1-(Phenylacetyl)-1,2,3,4-tetrahydrobenzo[c]-1,5-naphthyridine (prior art compounds) | $3.2 \times 10^{-4}$ |
| 9-amino-1,2,3,4-tetrahydroacridine (tacrine) | $5.7 \times 10^{-6}$ |
| Physostigmine | $9.2 \times 10^{-8}$ |

This utility is further demonstrated by the ability of these compounds to restore cholinergically deficient memory in the Dark Avoidance Assay, where they are in general active over a broader dose range than heretofore known compounds, a distinct therapeutic advantage.

DARK AVOIDANCE ASSAY

In this assay mice are tested for their ability to remember an unpleasant stimulus for a period of 24 hours. A mouse is placed in a chamber than contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic agent that is known to cause memory impairment, is administered before an animal's initial exposure to the test chamber, the animal re-enters the dark compartment shortly after being placed in the test chamber 24 hours later. This effect of scopolamine is blocked by an active test compound, resulting in greater interval before re-entry into the dark compartment.

The results for an active compound are expressed as the percent of a group of animals in which the effect of scopolamine is blocked, as manifested by an increased interval between being placed in the test chamber and re-entering the dark compartment.

| Compound | Dose (mg/kg of Body Weight) | % of Animals Greater than Scopolamine |
| --- | --- | --- |
| 1,2,3,4-Tetrahydro-benzo[c]-1,5-naphthyridine (prior art compounds) | 1.25 | 27 |
| | 2.5 | 25 |
| Tacrine | 0.63 | 13 |
| Pilocarpine | 5.0 | 13 |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, malic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contian, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention (including intermediate compounds which are believed to be novel) include:

(±)-1-[(3-Fluorophenyl)methyl]-5-methoxycarbonyl-2-pyrrolidinone;
(±)-1-[(3-Chlorophenyl)methyl]-5-methoxycarbonyl-1-pyrrolidinone;
(±)-1-[(4-Methoxyphenyl)methyl]-5-methoxycarbonyl-2-pyrrolidinone;
(±)-1-[(3-Methylphenyl)methyl]-5-methoxycarbonyl-2-pyrrolidinone
(±)-1-[(3-Fluorophenyl)methyl]-5-oxo-2-pyrrolidinecarboxylic acid;
(±)-1-[(3-Chlorophenyl)methyl]-5-oxo-2-pyrrolidinecarboxylic acid;
(±)-1-[(4-Methoxyphenyl)methyl]-5-oxo-2-pyrrolidinecarboxylic acid;
(±)-1-[(3-Methylphenyl)methyl]-5-oxo-2-pyrrolidinecarboxylic acid;
(±)-1-[(2-Trifluoromethylphenyl)methyl]-5-oxo-2-pyrrolidinecarboxylic acid;
1,10a-Dihydropyrrolo[1,2-b]isoquinoline-3,10[2H,5H]-dione;
1,10a-Dihydro-7-fluoropyrrolo[1,2-b]isoquinoline-3,10[2H,5H]-dione;
7-Chloro-1,10a-dihydropyrrolo[1,2-b]isoquinoline-3,10[2H,5H]-dione;
1,10a-Dihydro-8-methoxypyrrolo[1,2-b]isoquinoline-3,10[2H,5H]-dione;
9-Chloro-1,10a-dihydropyrrolo[1,2-b]isoiquinoline-3,10[2H,5H]-dione;
1,10a-Dihydro-7-methylpyrrolo[1,2-b]isoquinoline-3,10[2H,5H]-dione;
7,8-Dichloro-1,10a-dihydropyrrolo[1,2-b]isoquinoline-3,10[2H,5H]-dione;
1,10a-Dihydropyrrolo[1,2-b]isoquinoline-3,10[2H,5H]-dione oxime;
7-Chloro-1,10a-dihydropyrrolo[1,2-b]isoquinoline-3,10[2H,5H]-dione oxime;
8-Chloro-1,10a-dihydropyrrolo[1,2-b]isoquinoline-3,10[2H,5H]-dione oxime;
9-Chloro-1,10a-dihydropyrrolo[1,2-b]isoquinoline-3,10[2H,5H]-dione oxime;
1,10a-Dihydro-8-methoxypyrrolo[1,2-b]isoquinoline-3,10[2H,5H]-dione oxime;
1,10a-Dihydro-7-methylpyrrolo[1,2-b]isoquinoline-3,10[2H,5H]-dione oxime;
8-Bromo-1,10a-dihydropyrrolo[1,2-b]isoquinoline-3,10[2H,5H]-dione oxime;
7,8-Dichloro-1,10a-dihydropyrrolo[1,2-b]isoquinoline-3,10[2H,5H]-dione oxime;
1,4-Dihydrobenzo[c]-1,5-naphthyridin-2(3H)-one;
8-Chloro-1,4-dihydrobenzo[c]-1,5-naphthyridin-2(3H)-one;
9-Chloro-1,4-dihydrobenzo[c]-1,5-naphthyridin-2(3H)-one;
1,4-Dihydro-8-fluorobenzo[c]-1,5-naphthyridin-2(3H)-one;
9-Bromo-1,4-dihydrobenzo[c]-1,5-naphthyridin-2(3H)-one;
8,9-Dichloro-1,4-dihydrobenzo[c]-1,5-naphthyridin-2(3H)-one;
1,4-Dihydro-8-methylbenzo[c]-1,5-naphthyridin-2(3H)-one;
1,4-Dihydro-9-methoxybenzo[c]-1,5-naphthyridin-2(3H)-one;
3,4-Dihydro-2-methylaminobenzo[c]-1,5-naphthyridine;
3,4-Dihydro-2-(4-methyl-1-piperazinyl)benzo[c]-1,5-naphthyridine hemihydrate;
1,4-Dihydro-1-phenylmethylbenzo[c]-1,5-naphthyridin-2(3H)-one;
1,2,3,4-Tetrahydrobenzo[c]-1,5-naphthyridine;
8-Chloro-1,2,3,4-tetrahydrobenzo[c]-1,5-naphthyridine;
9-Chloro-1,2,3,4-tetrahydrobenzo[c]-1,5-naphthyridine;
8-Fluoro-1,2,3,4-tetrahydrobenzo[c]-1,5-naphthyridine;
9-Bromo-1,2,3,4-tetrahydrobenzo[c]-1,5-naphthyridine;
8-Methyl-1,2,3,4-tetrahydrobenzo[c]-1,5-naphthyridine;
9-Methoxy-1,2,3,4-tetrahydrobenzo[c]-1,5-naphthyridine;
8,9-Dichloro-1,2,3,4-tetrahydrobenzo[c]-1,5-naphthyridine;
1-Formyl-1,2,3,4-tetrahydrobenzo[c]-1,5-naphthyridine;
1-Benzoyl-1,2,3,4-tetrahydrobenzo[c]-1,5-naphthyridine;

1-(Phenylacetyl)-1,2,3,4-tetrahydrobenzo[c]-1,5-naphthyridine;
1-(2-Bromopropionyl)-1,2,3,4-tetrahydrobenzo[c]-1,5-naphthyridine;
1-(2-Aminopropionyl)-1,2,3,4-tetrahydrobenzo[c]-1,5-naphthyridine;
1-[(2-Fluorophenyl)acetyl]-1,2,3,4-tetrahydrobenzo[c]-1,5-naphthyridine;
1-[(2-Chlorophenyl)acetyl]-1,2,3,4-tetrahydrobenzo[c]-1,5-naphthyridine;
1-[(4-Chlorophenyl)acetyl]-1,2,3,4-tetrahydrobenzo[c]-1,5-naphthyridine;
1-[(2-Methoxyphenyl)acetyl]-1,2,3,4-tetrahydrobenzo[c]-1,5-naphthyridine;
1-[(4-Methoxyphenyl)acetyl]-1,2,3,4-tetrahydrobenzo[c]-1,5-naphthyridine;
1-(2-Thienyl)acetyl-1,2,3,4-tetrahydrobenzo[c]-1,5-naphthyridine;
1-(3-Thienyl)acetyl-1,2,3,4-tetrahydrobenzo[c]-1,5-naphthyridine;
1-Methyl-1,2,3,4-tetrahydrobenzo[c]-1,5-naphthyridine;
1-(2-Phenylethyl)-1,2,3,4-tetrahydrobenzo[c]-1,5-naphthyridine;
1-phenylmethyl-1,2,3,4-tetrahydrobenzo[c]-1,5-naphthyridine;
1-[3-(Phenyl)propyl]-1,2,3,4-tetrahydrobenzo[c]-1,5-naphthyridine;
1-[2-(2-Fluorophenyl)ethyl]-1,2,3,4-tetrahydrobenzo[c]-1,5-naphthyridine;
1-[2-(2-Chlorophenyl)ethyl]-1,2,3,4-tetrahydrobenzo[c]-1,5-naphthyridine;
1-[2-(4-Chlorophenyl)ethyl]-1,2,3,4-tetrahydrobenzo[c]-1,5-naphthyridine;
1-[2-(2-Methoxyphenyl)ethyl]-1,2,3,4-tetrahydrobenzo[c]-1,5-naphthyridine;
1-[2-(4-Methoxyphenyl)ethyl]-1,2,3,4-tetrahydrobenzo[c]-1,5-naphthyridine;
1-[2-(2-Thienyl)ethyl]-1,2,3,4-tetrahydrobenzo[c]-1,5-naphthyridine; and
1-[2-(3-Thienyl)ethyl]-1,2,3,4-tetrahydrobenzo[c]-1,5-naphthyridine.

The following examples are shown for the purpose of illustrating the present invention.

EXAMPLE 1

($\pm$)-1-[(3-Fluorophenyl)methyl]-5-methoxycarbonyl-2-pyrrolidinone

Sodium hydride (24.00 g as a 50% dispersion in mineral oil) was washed with sieve dried toluene (3×100 ml). Sieve dried toluene (500 ml) was then added to the NaH and the stirred suspension was treated dropwise over 45 minutes with a solution of ($\pm$)-methyl pyroglutamate (71.58 g) in sieve dried toluene (50 ml). The flask was immersed during this time in an oil bath which served as a heat sink. After the addition of the ($\pm$)-methyl pyroglutamate solution was complete, the internal temperature of the flask was raised to 65° C. and maintained there for 30 minutes. The flask was then cooled to the ambient temperature and the solution was treated dropwise over 10 minutes with a solution of 3-fluorobenzyl bromide (100 g) in sieve dried toluene (50 ml). After the addition was complete, the internal temperature of the flask was raised to 90° C. and maintained there until a thin layer chromatographic analysis (TLC analysis hereafter) using silica gel and ethyl acetate indicated the absence of the starting material. While still hot, the suspension was vacuum filtered through a Celite pad and concentrated to an oil (90 g) which solidified on standing. The solid was recrystallized from hexane (100 ml) to afford 78.69 g of nearly pure crystals, m.p. 46°–51° C. A 6 g sample was recrystallized from hexane (30 ml) to give 5.31 g of crystals, m.p. 52°–55° C.

ANALYSIS: Calculated for $C_{13}H_{14}FNO_3$: 62.12%C, 5.62%H, 5.58%N. Found: 61.72%C, 5.55%H, 5.60%N.

EXAMPLE 2

($\pm$)-1-[(3-Chlorophenyl)methyl]-5-methoxycarbonyl-2-pyrrolidinone

Sodium hydride (23.38 g of a 50% dispersion in mineral oil) was washed with sieve dried toluene. Sieve dried toluene (1000 ml) was then added to the NaH and the stirred suspension was treated dropwise over 45 minutes with a solution of ($\pm$)-methyl pyroglutamate (63.0 g) in sieve dried toluene (75 ml). The flask was immersed during this time in an oil bath which served as a heat sink. After the addition of the ($\pm$)-methyl pyroglutamate solution was complete, the bath temperature was raised to 65° C. After heating for 30 minutes, the oil bath was removed and the solution was treated dropwise over 10 minutes with a solution of 3-chloro-benzyl bromide (100 g) in sieve dried toluene (50 ml). After the addition was complete, the oil bath was replaced and the solution was heated for 2 hours at 100° C. Celite was then added to the mixture and while still hot, the mixture was vacuum filtered through a Celite pad. The filtrate was concentrated to an oil which was stored in a refrigerator under nitrogen.

Purification of 11.20 g of the oil by high performance liquid chromatography (HPLC, hereafter) using silica gel column and methanol gave 8.10 g of an oil. The sample was dried in an Abderhalden pistol over toluene.

ANALYSIS: Calculated for $C_{13}H_{14}ClNO_3$: 58.33%C, 5.27%H, 5.23%N. Found: 58.13%C, 5.30%H, 5.17%N.

EXAMPLE 3

($\pm$)-1-[(4-Methoxyphenyl)methyl]-5-methoxycarbonyl-2-pyrrolidinone

Sodium hydride (27.84 g of a 50% dispersion in mineral oil) was washed with sieve dried toluene (3×100 ml). Sieve dried toluene (500 ml) was then added to the NaH and the stirred suspension was treated dropwise over 45 minutes with a solution of ($\pm$)methyl pyroglutamate (83.03 g) in sieve dried toluene (50 ml). The flask was immersed during this time in an oil bath which served as a heat sink. After the addition of the ($\pm$)methyl pyroglutamate solution was complete, the bath temperature was raised to 80° C. (internal temperature 65° C.). After heating for 30 minutes, the flask was cooled to room temperature and the solution was treated dropwise over 10 minutes with a solution of 4-methoxybenzyl chloride (100 g) in sieve dried toluene (50 ml). After the addition was complete, the mixture was heated to 85° C. (internal temperature). While still hot, the mixture was vacuum filtered and the filtrate was concentrated to an oil.

Purification of 10 g of the oil was accomplished by HPLC (silica gel column, eluted with ethyl acetate) to give 4.85 g of an oil. The sample was dried in an Abderhalden pistol over toluene.

ANALYSIS: Calculated for $C_{14}H_{17}NO_4$: 63.84%C, 6.51%H, 5.32%N. Found: 63.62%C, 6.71%H, 5.04%N.

EXAMPLE 4

(±)-1-[(3-Fluorophenyl)methyl]-5-oxo-2-pyrrolidinecarboxylic acid

A solution of 19.00 g of sodium hydroxide pellets in 225 ml of water was treated with 115.52 g of (±)-1-[(3-fluorophenyl)methyl]-5-methoxycarbonyl-2-pyrrolidinone and the mixture was heated for four hours (steam bath). The solution was cooled to the ambient temperature and extracted with diethyl ether (3×250 ml). The aqueous phase was acidified with concentrated hydrochloric acid to about pH=1. The aqueous phase was extracted with dichloromethane (2×300 ml) and the combined organic phase was dried over $Na_2SO_4$. The solution was vacuum filtered and the filtrate was concentrated to an oil which solidified on standing. The solid was recrystallized from 300 ml of toluene to yield 72.16 g of crystals, m.p. 114°–116.5° C.

ANALYSIS: Calculated for $C_{12}H_{12}FNO_3$: 60.73%C, 5.10%H, 5.91%N. Found: 60.51%C, 5.20%H, 5.77%N.

EXAMPLE 5

(±)-1-[(3-Chlorophenyl)methyl]-5-oxo-2-pyrrolidinecarboxylic acid

A solution of 16.00 g of sodium hydroxide pellets in 165 ml of water was treated with 99.01 g of (±)-1-[(3-chlorophenyl)methyl]-5-methoxycarbonyl-2-pyrrolidinone and was heated for two hours with a steam bath. The solution was cooled to room temperature and extracted with diethyl ether (2×300 ml). The aqueous phase was acidified with 45 ml of concentrated hydrochloric acid and extracted with dichloromethane (3×200 ml). Crystals precipitated out of the dichloromethane. The crystals (80.21 g, damp with solvent) were dried overnight at 65° C. under vacuum.

The solid was recrystallized from 800 ml of toluene to give 54.72 g of crystals m.p. 144°–146° C. The crystals were dried overnight at 85° C. under vacuum.

ANALYSIS: Calculated for $C_{12}H_{12}ClNO_3$: 56.79%C, 4.77%H, 5.53%N. Found: 57.05%C, 4.80%H, 5.49%N.

EXAMPLE 6

(±)-1-[(4-Methoxyphenyl)methyl]-5-oxo-2-pyrrolidinecarboxylic acid

A solution of 16.80 g of sodium hydroxide pellets in 175 ml of water was treated with 75 g of (±)-1-[(4-methoxyphenyl)methyl]-5-methoxycarbonyl-2-pyrrolidinone and the mixture was heated for two hours with a steam bath. The solution was cooled to room temperature and extracted with diethyl ether (2×300 ml). The aqueous phase was acidified to about pH=1 with 50 ml of concentrated hydrochloric acid and extracted with dichloromethane (3×250 ml). the dried ($Na_2SO_4$) organic phase was vacuum filtered and concentrated to an oil which solidified on standing (80 g). The solid was recrystallized from toluene (300 ml) to give 34.18 g of crystals, m.p. 103°–104.5° C.

ANALYSIS: Calculated for $C_{13}H_{15}NO_4$: 62.62%C, 6.07%H, 5.62%N. Found: 62.48%C, 6.05%H, 5.54%N.

EXAMPLE 7

1,10a-Dihydropyrrolo[1,2-b]isoquinoline-3,10[2H,5H]-dione

To a solution prepared from 11.68 g of (±)-N-benzylpyroglutamic acid (See. E. Campaigne and D. P. Matthews, J. Het. Chem., 12, 391 (1975)), 100 ml of $CH_2Cl_2$ and a drop of dimethylformamide (DMF), 7.57 g of $SOCl_2$ was added dropwise. The mixture was refluxed for five hours and allowed to stand overnight at ambient temperature. The reaction mixture was cooled in an ice-salt bath. Aluminum chloride (22.6 g) was added in portions with exclusion of moisture and vigorous stirring. The temperature did not exceed 10° C. during the addition. The mixture was stirred 1.5 hours and then ice was added gradually. The mixture was partitioned between water and $CH_2Cl_2$. The $CH_2Cl_2$ phase was washed with water, dried ($Na_2SO_4$), filtered and evaporated to give 10 g of a crude product. Recrystallization from toluene gave 7.45 g of crystals, m.p. 103°–105° C.

ANALYSIS: Calculated for $C_{12}H_{11}NO_2$: 71.62%C, 5.51%H, 6.96%N. Found: 71.36%C, 5.43%H, 6.85%N.

EXAMPLE 8

1,10a-Dihydro-7-fluoropyrrolo[1,2-b]isoquinoline-3,10[2H,5H]-dione

To a solution of 50.00 g of (±)-1-[(3-fluorophenyl)methyl]-5-oxo-2-pyrrolidine carboxylic acid in sieve dried dichloromethane (450 ml), 27.48 g of thionyl chloride was added, and the resultant solution was stirred and refluxed for 5 hours. An infrared spectrum of the solution indicated the presence of the acid chloride. After standing overnight at ambient temperature, the solution was chilled to 5° C. and 84 g of aluminum chloride was added in portions with vigorous stirring. The reaction was exothermic and there was a slow evolution of gas. The mixture was stirred at ambient temperature for 3 hours. The reaction was quenched by the addition of ice chips and water. The two phases of the mixture were separated and the aqueous phase was extracted with dichloromethane (4×150 ml). The combined organic phase was dried ($Na_2SO_4$) and concentrated to a solid (69.73 g).

The solid was purified by HPLC (silica gel, eluted with ethyl acetate) to give 37.23 g of the 7-fluoro isomer and 4 g of the 9-fluoro isomer. The 7-fluoro isomer was recrystallized from ethyl acetate (400 ml) to afford 28.63 g of crystals, m.p. 160°–163° C.

ANALYSIS: Calculated for $C_{12}H_{10}FNO_2$: 65.70%C, 4.60%H, 6.39%N. Found: 65.60%C, 4.68%H, 6.27%N.

EXAMPLE 9

7-Chloro-1,10a-dihydropyrrolo[1,2-b]isoquinoline-3,10[2H,5H]-dione

To a solution of 25.37 g of (±)-1-[(3-chlorophenyl)methyl]-5-oxo-2-pyrrolidinecarboxylic acid in sieve dried dichloromethane (20 ml), 13.09 g of thionyl chloride was added, and the resultant solution was stirred and refluxed with the exclusion of moisture for 6 hours. An infrared spectrum of the solution indicated the presence of the acid chloride. After standing overnight at ambient temperature, the solution was chilled to 5° C. and 40 g of aluminum chloride was added in portions with exclusion of moisture and vigorous stirring. The reaction was slightly exothermic and a solid began to precipitate. The flask was heated intermittently with a steam bath to increase the rate of the reaction. After each heating, the gas evolution was allowed to subside. When heating did not produce gas evolution, ice chips were added to quench the reaction. Water was then added to the mixture and the phases were separated. The aqueous phase was extracted with dichloromethane and the combined organic phase was dried ($Na_2$-

SO₄). The mixture was vacuum filtered and concentrated to a solid to which ethyl acetate was added and the resultant mixture was vacuum filtered to give 11.56 g of a solid. The solid was dried overnight under vacuum.

The ethyl acetate washings were concentrated to 10.30 g of a solid. A TLC analysis (silica, ethyl acetate) showed that the compositions of the two crops of solid were the same. The combined solid was purified by HPLC (silica gel, eluted with ethyl acetate) to give 16.35 g of a solid which was recrystallized from ethyl acetate (250 ml) to yield 12.0 g of a solid, m.p. 150.5°–154° C.

ANALYSIS: Calculated for $C_{12}H_{10}ClNO_2$: 61.16%C, 4.28%H, 5.94%N. Found: 60.79%C, 4.41%H, 5.89%N.

EXAMPLE 10

9-Chloro-1,10a-dihydropyrrolo[1,2-b]isoquinoline-3,10[2H,5H]-dione

9-Chloro-1,10a-dihydropyrrolo[1,2-b]isoquinoline-3,10[2H,5H]-dione was isolated by HPLC (silica gel, ethyl acetate) as the minor product from the reaction which afforded 7-chloro-1,10a-dihydropyrrolo[1,2-b]isoquinoline-3,10[2H,5H]-dione. From two runs of the reaction, a total of 3.55 g of the 9-chloro isomer was obtained and recrystallized from 100 ml of ethyl acetate to afford 2.03 g of crystals, m.p. 198°–202° C.

ANALYSIS: Calculated for $C_{12}H_{10}ClNO_2$: 61.16%C, 4.28%H, 5.94%N. Found: 60.79%C, 4.38%H, 5.83%N.

EXAMPLE 11

1,10a-Dihydropyrrolo[1,2-b]isoquinoline-3,10[2H,5H]-dione oxime

A mixture consisting of 2.5 g of 1,10a-dihydropyrrolo[1,2-b]isoquinoline-3,10[2H,5H]-dione in 20 ml of 95% ethanol (EtOH), 1.72 g of hydroxylamine hydrochloride in 10 ml of water and 3.7 g of sodium acetate trihydrate in 10 ml of water was refluxed for 7 hours and thereafter allowed to stand overnight at ambient temperature. The product crystallized from the reaction mixture to give 2.2 g of crystals. Recrystallization from 95% EtOH gave 1.4 g of crystals, m.p. 206°–209° C.

ANALYSIS: Calculated for $C_{12}H_{12}N_2O_2$: 66.65%C, 5.60%H, 12.95%N. Found: 66.36%C, 5.59%H, 12.93%N.

EXAMPLE 12

7-Chloro-1,10a-dihydropyrrolo[1,2-b]isoquinoline-3,10[2H,5H]-dione oxime

A suspension of 9.00 g of 7-chloro-1,10a-dihydropyrrolo[1,2-b]isoquinoline-3,10[2H,5H]-dione in 95% ethanol (65 ml) was treated with a premixed solution prepared from 10.40 g of sodium acetate trihydrate in water (35 ml) and 5.31 g of hydroxylamine hydrochloride in water (35 ml). The suspension was heated to reflux and after 10 minutes a solution formed. After 1 hour of refluxing, a precipitate began to form and heating was continued for another 1.5 hours, after which time the mixture was allowed to cool to ambient temperature. The precipitate was isolated by vacuum filtration and dried under vacuum at 40° C. The solid was recrystallized form n-propanol (300 ml) to give 6.45 g of crystals, m.p. 249°–252° C.

ANALYSIS: Calculated for $C_{12}H_{11}ClN_2O_2$: 57.50%C, 4.42%H, 11.17%N. Found: 57.33%C, 4.51%H, 11.11%N.

EXAMPLE 13

8-Chloro-1,10a-dihydropyrrolo[1,2-b]isoquinoline-3,10[2H,5H]-dione oxime

A stirred suspension of 12.65 g of 8-chloro-1,10a-dihydropyrrolo[1,2-b]isoquinoline-3,10[2H,5H]-dione (prepared in substantially the same manner as the 7-chloro compound in Example 12, m.p. 130°–136° C.) in 95% ethanol (85 ml) was treated with a premixed solution prepared from sodium acetate trihydrate (14.56 g) in water (48 ml) and hydroxylamine hydrochloride (7.44 g) in water (48 ml). The stirred suspension was heated to reflux, during which a solution formed followed by separation of a crystalline precipitate. After 2 hours of refluxing, the mixture was cooled and the precipitate was collected and washed twice with 50% aqueous ethanol. Drying at 40° C. overnight in vacuo gave 10.95 g of a solid, m.p. 227.5°–230.5° C. Recrystallization of the solid from n-propanol (300 ml) afforded 8.56 g of crystals, m.p. 229°–235° C.

ANALYSIS: Calculated for $C_{12}H_{11}ClN_2O_2$: 57.50%C, 4.42%H, 11.17%N. Found: 57.18%C, 4.41%H, 11.21%N.

EXAMPLE 14

9-Chloro-1,10a-dihydropyrrolo[1,2-b]isoquinoline-3,10[2H,5H]-dione oxime

A suspension of 1.00 g of 9-chloro-1,10a-dihydropyrrolo[1,2-b]isoquinoline-3,10[2H,5H]-dione in 95% ethanol (10 ml) was treated with a premixed solution prepared from 1.17 g of sodium acetate trihydrate in water (5 ml) and 0.60 g of hydroxylamine hydrochloride in water (5 ml). The suspension was heated to reflux and after 15 minutes a solution formed. After 1 hour of reflux, a precipitate began to form. Heating was continued for another 1.5 hours, after which time the mixture was allowed to cool to ambient temperature. The precipitate was isolated by vacuum filtration and dried under vacuum at 40° C.

The solid (0.75 g) was combined with 0.92 g of a material obtained in similar manner and recrystallized from 95% ethanol (100 ml) to afford 1.25 g of crystals, m.p. 260°–265° C.

ANALYSIS: Calculated for $C_{12}H_{11}ClN_2O_2$: 57.50%C, 4.42%H, 11.17%N. Found: 57.55%C, 4.40%H, 11.04%N.

EXAMPLE 15

1,4-Dihydrobenzo[c]-1,5-naphthyridin-2(3H)-one

To 300 g of vigorously stirred polyphosphoric acid warmed to 115° C., 10 g of 1,10a-dihydropyrrolo[1,2-b]-isoquinoline-3,10[2H,5H]-dione oxime was added. The mixture was held at this bath temperature for 10 minutes. The internal temperature rose to 135°–140° C. The mixture was then poured into 1500 ml of ice water, and the mixture was basified with 50% NaOH to about pH=8 and the resultant crystalline precipitate was collected to give 7.14 g of crude product. Chromatography on a silica gel column, using ethyl acetate gave 4.8 g of pure product, m.p. 225° C.

ANALYSIS: Calculated for $C_{12}H_{10}N_2O$: 72.69%C, 5.08%H, 14.13%N. Found: 72.53%C, 5.26%H, 14.14%N.

EXAMPLE 16

8-Chloro-1,4-dihydrobenzo[c]-1,5-naphthyridin-2(3H)-one

To 110 g of vigorously stirred polyphosphoric acid, which had been heated to 105° C., 10.21 g of 7-chloro-1,10a-dihyropyrrolo[1,2-b]isoquinoline-3,10[2H,5H]-dione oxime was added. The bath temperature was held at 105° C. for 25 minutes. On addition of the oxime, however, the internal temperature rose to 145° C. The reaction was quenched by pouring the mixture into 800 ml of water and subsequently another 300 ml of water was added to the mixture. The mixture was basified to about pH=11 with 50% sodium hydroxide at which point precipitate began to separate from the mixture. Due to a large amount of inorganic phosphate salts formed, the mixture was diluted with water to approximately 20 liters. The precipitate was collected by vacuum filtration and dried overnight under vacuum at 60° C.

The solid was recrystallized from 1200 ml of n-propanol to afrord 6.1 g of crystals, m.p. 281°–284° C. The crystals were dried under vacuum overnight at 50° C.

ANALYSIS: Calculated for $C_{12}H_9ClN_2O$: 61.89%C, 3.90%H, 12.04%N. Found: 62.00%C, 3.97%H, 12.00%N.

EXAMPLE 17

9-Chloro-1,4-dihydrobenzo[c]-1,4-naphthyridin-2(3H)-one

To stirred hot (100° C.) polyphosphoric acid (70 g) was added finely powdered 8-chloro-1,10a-dihydropyrrolo[1,2-b]-isoquinoline-3,10[2H,5H]-dione oxime (5.01 g) in one portion. An exothermic reaction initiated and quickly subsided. Fourteen minutes after the addition of the oxime, the reaction mixture was decanted into water (250 ml). The suspension was diluted with water to approximately 400 ml of total volume and basified with 50% sodium hydroxide solution with cooling. The mixture was extracted with $CH_2Cl_2$ (2000 ml), dried ($Na_2SO_4$), filtered and concentrated to give 5.3 g of a solid. The material was purified by HPLC (silica gel, eluted with ethyl acetate) to give 4.5 g of a solid. Recrystallization from n-propanol gave 2.92 g of crystals, m.p. 285°–286° C.

ANALYSIS: Calculated for $C_{12}H_9ClN_2O$: 61.95%C, 3.90%H, 12.04%N. Found: 61.97%C, 3.92%H, 11.99%N.

EXAMPLE 18

3,4-Dihydro-2-methylaminobenzo[c]-1,5-naphthyridine

A solution of anhydrous methylamine (30 ml), 1,4-dihydrobenzo[c]-1,5-naphthyridin-2(3H)-one (5.46 g) and sieve dried tetrahydrofuran (450 ml) was stirred and chilled with ice water, and was treated dropwise over 30 minutes with a preformed complex of titanium tetrachloride (3.0 ml, 5.2 g) and sieve dried tetrahydrofuran (220 ml). The resultant mixture was stirred with cooling for 1 hour, followed by stirring for 3.5 hours at ambient temperature. After standing overnight at ambient temperature the reaction was quenched with water (100 ml) and 10% NaOH solution (30 ml). The suspension was filtered and concentrated to give a biphasic residue (pH 10). The mixture was extracted with dichloromethane (2×200 ml) dried ($Na_2SO_4$), filtered and evaporated to dryness (residue wt: 7.66 g). The residue was purified by HPLC (silica gel, eluted with 10% (v/v) methanol in ethyl acetate). The appropriate fractions were concentrated to give 5.1 g of pure product which was recrystallized from toluene (35 ml) to afford 3.56 g of crystals, m.p. 144°–145° C.

ANALYSIS: Calculated for $C_{13}H_{13}N_3$: 73.91%C, 6.20%H. Found: 73.74%C, 6.15%H.

EXAMPLE 19

3,4-Dihydro-2-(4-methyl-1-piperazinyl)benzo[c]-1,5-naphthyridine hemihydrate

A complex of $TiCl_4$ and tetrahydrofuran was prepared by dropwise treatment via syringe of tetrahydrofuran (200 ml) with $TiCl_4$ (2.8 ml, 4.84 g) with stirring and ice water chilling (exclusion of moisture). The resultant suspension was treated with tetrahydrofuran (50 ml) to give a solution of the complex which was transferred to a dropping funnel (without side arm). A stirred, ice water chilled solution of 1,4-dihydrobenzo[c]-1,5-naphthyridine-2(3H)-one (3.39 g), tetrahydrofuran (275 ml) and 1-methylpiperazine (34 ml) was treated dropwise over 35 minutes with the $TiCl_4$-tetrahydrofuran complex with exclusion of moisture. The mixture was then stirred overnight at ambient temperature. The reaction was quenched by addition of water (100 ml) over approximately one minute. The resultant mixture was filtered through coarse-grade fluted filter paper and the filtrate was concentrated to remove the tetrahydrofuran. After basification with 10% NaOH and extraction with $CH_2Cl_2$ (2×250 ml), the dried ($Na_2SO_4$) organic phase was filtered and evaporated to afford an oil (5.17 g) which contained several components by TLC (silica gel, methanol) analysis. The oil was purified by HPLC (silica gel, eluted with methanol) to give 3.93 g of a viscous oil which appeared pure by TLC (silica gel, methanol). This sample and another sample prepared in a similar manner were combined and repurified by HPLC as described above to give 4.48 g of an oil which appeared pure by TLC (silica gel, methanol).

ANALYSIS: Calculated for $C_{17}H_{20}N_4.0.5H_2O$: 70.56%C, 7.32%H. Found: 70.05%C, 7.31%H.

EXAMPLE 20

1,4-Dihydro-1-phenylmethylbenzo[c]-1,5-naphthyridin-2(3H)-one

A stirred solution of 1,4-dihydrobenzo[c]-1,5-naphthyridin-2(3H)-one (3.97 g) in dimethylsulfoxide (sieve dried, 80 ml) was treated sequentially with powdered potassium hydroxide (2.64 g of 85% KOH) and benzyl bromide (3.76 g). The solution was stirred for 1.5 hours at ambient temperature, transferred to a separatory funnel, diluted with water (400 ml) and extracted with ethyl acetate (2×250 ml). The organic phase was washed with water (2×200 ml), dried ($Na_2SO_4$), filtered and evaporated to give a solid (4.9 g). Recrystallization from 95% ethanol (32 ml) gave 3.35 g of crystals, m.p. 153.5°–155.5° C.

ANALYSIS: Calculated for $C_{19}H_{16}N_2O$: 79.14%C, 5.59%H, 9.71%N. Found: 78.95%C, 5.65%H, 9.65%N.

EXAMPLE 21

1,2,3,4-Tetrahydrobenzo[c]-1,5-naphthyridine

A stirred solution of 1,4-dihydrobenzo[c]-1,5-naphthyridin-2(3H)-one (4.0 g) in sieve dried tetrahydrofuran (400 ml) was treated over a few minutes with 0.98M borane in tetrahydrofuran (62 ml) under a dry nitrogen atmosphere. The resultant suspension was stirred for 5 hours at ambient temperature during which time a solution formed. After standing overnight at ambient temperature the solution was treated with glacial acetic acid (16 ml) followed by stirring for several minutes. The solution was then treated with 10% sodium hydroxide solution (180 ml) to give a biphasic system. Concentration on a rotary evaporator to remove the tetrahydrofuran gave a suspension of a solid which was extracted with $CH_2Cl_2$ (2×800 ml). The combined, dried ($Na_2SO_4$) organic phase was concentrated to afford a solid (5.18 g, tentatively identified as a borane complex). A suspension of the solid in glacial acetic acid (15 ml) was treated gradually with concentrated HCl (50 ml). When the gas evolution ceased, the mixture was warmed for a few minutes and then stirred for 0.5 hour at ambient temperature. The solution was strained through glass wool, and the filtrate was diluted with ice (300 ml) and water (100 ml) and then made alkaline with 50% sodium hydroxide solution. The mixture was extracted with $CH_2Cl_2$, dried ($Na_2SO_4$), filtered and concentrated to dryness (3.7 g). Recrystallization from acetonitrile (20 ml) gave 1.97 g of a crystalline material which was combined with 2.01 g of a similarly prepared product. The material was purified by HPLC (silica gel, eluted with 5% methanol in ethyl acetate) to give 3.72 g of a solid. Recrystallization from acetonitrile (20 ml) afforded 3.01 g of crystals, m.p. 124.5°–127.5° C.

ANALYSIS: Calculated for $C_{12}H_{12}N_2$: 78.23%C, 6.57%N. Found: 77.91%C, 6.56%N.

EXAMPLE 22

9-Chloro-1,2,3,4-tetrahydrobenzo[c]-1,5-naphthyridine

A stirred suspension of 9-chloro-1,4-dihydrobenzo[c]-1,5-naphthyridin-2(3H)-one (5.82 g) in sieve dried tetrahydrofuran (600 ml) was treated rapidly with 1M borane in tetrahydrofuran (150 ml) and the resultant solution was stirred 48 hours at ambient temperature. The solution was treated dropwise with 10% sodium hydroxide solution (125 ml) (gas evolution noted), concentrated to remove the tetrahydrofuran and the residual suspension was filtered. The filter cake (a borane complex of the product) was suspended in glacial acetic acid (40 ml) and was treated under nitrogen with concentrated hydrocholoric acid (35 ml, gas evolution noted). After stirring for 1 hour at ambient temperature the solution was decanted over crushed ice (500 ml), diluted with water (100 ml) and basified with 50% sodium hydroxide solution. The resultant suspension was extracted with dichloromethane (2×350 ml) and the combined dried ($Na_2SO_4$) organic phase was evaporated to afford a solid (5.84 g). A TLC analysis (silica gel, ethyl acetate) indicated the presence of a major product and three impurities. The material was purified by HPLC (silica gel, eluted with ethyl acetate) to afford 4.64 g of a purified material. Recrystallization from acetonitrile (125 ml) gave 3.54 g of needles, m.p. 185°–186° C.

ANALYSIS: Calculated for $C_{12}H_{11}ClN_2$: 65.91%C, 5.07%H, 12.81%N. Found: 65.88%C, 5.19%H, 12.90%N.

EXAMPLE 23

1-Formyl-1,2,3,4-tetrahydrobenzo[c]-1,5-naphthyridine

Formic-acetic anhydride was prepared by treating 30 ml of acetic anhydride with 13.5 ml of 95–97% formic acid and stirring the resultant solution at 50° C. for 40 minutes. 1,2,3,4-Tetrahydrobenzo[c]-1,5-naphthyridine (5.0 g) was added to the solution in one portion followed by heating at 86° C. for 3.5 hours. A vigorous gas evolution was noted during the first hour of heating. A TLC analysis (silica gel, 10% methanol in ethyl acetate) suggested the presence of the starting material and the solution was held at 100° C. overnight. The cooled reaction solution was decanted into 300 ml of ice water and basified with 50% NaOH solution. After $CH_2Cl_2$ extraction (2×150 ml), the combined and dried ($Na_2SO_4$) organic phase was filtered and concentrated to an oil which still contained the starting material by TLC analysis. The mixed anhydride prepared from acetic anhydride (60 ml) and 95–97% formic acid (27 ml) was added to the oil and the solution was stirred at 58° C. Again gas evolution was noted. The solution was stirred for 2 hours at 85° C. (gas evolution subsided) and then quenched as described above. A TLC analysis indicated the absence of the starting material. Recrystallization of the crude product (5.2 g) from hot toluene (10 ml) by diluting the filtered solution gradually with cyclohexane (45 ml) and seeding gave 3.02 g of crystals, m.p. 85°–88° C.

ANALYSIS: Calculated for $C_{13}H_{12}N_2O$: 73.57%C, 5.70%H, 13.20%N. Found: 73.88%C, 5.99%H, 13.19%N.

EXAMPLE 24

1-Benzoyl-1,2,3,4-tetrahydrobenzo[c]-1,5-naphthyridine

A stirred solution of 1,2,3,4-tetrahydrobenzo[c]-1,5-naphthyridine (4.6 g) and KOH-dried pyridine (50 ml) was treated dropwise over one minute with benzoyl chloride (8.4 g). A crystalline precipitate formed. The stirred suspension was heated (steam bath) for 1.25 hours and the resultant solution was then stirred overnight at ambient temperature during which a crystalline precipitate formed. The mixture was decanted into water (200 ml), basified with 10% sodium hydroxide solution and extracted with dichloromethane. The dried ($Na_2SO_4$) organic phase was filtered and evaporated to dryness (7.47 g of crystalline solid). Recrystallization from toluene afforded 6.25 g of crystals, m.p. 208.5°–210.5° C. An aliquot of the material (4.81 g) was further purified by preparative HPLC (silica gel, eluted with ethyl acetate). The appropriate fractions were concentrated and the residue was recrystallized from toluene (100 ml) to give 4.14 g of crystals, m.p. 208°–210° C.

ANALYSIS: Calculated for $C_{19}H_{16}N_2O$: 79.14%C, 5.59%H, 9.71%N. Found: 79.08%C, 5.82%H, 9.58%N.

EXAMPLE 25

1-(Phenylacetyl)-1,2,3,4-tetrahydrobenzo[c]-1,5-naphthyridine 1,2,3,4-Tetrahydrobenzo[c]-1,5-naphthyridine (3.22 g) was treated with cold phenylacetyl chloride (35 ml). Most of the material dissolved and then a precipitate separated. The mixture was diluted with ether (50 ml), and the precipitate was isolated by vacuum filtration and washed twice with ether. The filter cake was dissolved in water (100 ml), and the solution was basified with 10% sodium hydroxide solution and extracted with dichloromethane (2×100 ml). The combined and dried ($Na_2SO_4$) organic phase was filtered and concentrated to an oil (5.4 g), which was purified by HPLC (silica gel, eluted with ethyl acetate). The appropriate fractions were combined and concentrated to an oil (4.76 g). Trituration with ether and seeding (seed crystals formed on the neck of the flask which contained the oil) gave 2.68 g of crystals, m.p. 88.5°–89.5° C.

ANALYSIS: Calculated for $C_{20}H_{18}N_2O$: 79.45%C, 6.00%H, 9.26%N. Found: 79.50%C, 6.10%H, 9.25%N.

EXAMPLE 26

1-Methyl-1,2,3,4-tetrahydrobenzo[c]-1,5-naphthyridine dihydrochloride

A solution of 1-formyl-1,2,3,4-tetrahydrobenzo[c]-1,5-naphthyridine (9.6 g) in sieve dried tetrahydrofuran (1000 ml) was treated under nitrogen over 60 seconds with excess 1M borane-tetrahydrofuran complex (175 ml). After stirring for 48 hours at ambient temperature, the solution was treated dropwise with 10% sodium hydroxide solution (vigorous gas evolution during initial addition of NaOH) to give a biphasic liquid which was concentrated to remove the tetrahydrofuran. The residual oil-water mixture was extracted with $CH_2Cl_2$ (2×300 ml) and the combined and dried ($Na_2SO_4$) organic phase was filtered and concentrated to an oil (a borane complex). A solution of the oil in glacial acetic acid (25 ml) was treated gradually with concentrated hydrochloric acid (35 ml) under $N_2$ purge. After stirring for 0.5 hours at ambient temperature, the solution was decanted onto ice chips (500 ml), diluted with water (300 ml) and made alkaline with 50% sodium hydroxide solution. Extraction with $CH_2Cl_2$ (2×300 ml) and concentration of the dried ($Na_2SO_4$) organic phase gave a mobile oil (7.59 g). The oil contained three significant impurities and the desired product according to a TLC analysis (silica gel, ethyl acetate). Initial purification was conducted by HPLC (silica gel, eluted with ethyl acetate) to give 1.85 g of a two component oil (1,2,3,4-tetrahydrobenzo[c]-1,5-naphthyridine and the desired product). A further HPLC purification in a similar manner utilizing the recycle technique to optimize the separation gave 1.66 g of the product as an oil. The product was combined with 1.38 g of a similarily prepared material, and a methanol solution of the oils was treated with excess ethereal hydrogen chloride. Concentration of the resultant solution gave 3.44 g of a crude material which was recrystallized from absolute ethanol (150 ml) to give 0.82 g of crystals. Concentration of the mother liquor and recrystallization of the residue from absolute ethanol (100 ml) give 1.43 g of crystals. The two lots of the material were combined, after a TLC analysis (silica gel, methanol) had confirmed the identity, to give 2.25 g of crystals, m.p. 206°–208° C. (transition with gas evolution), 261°–272° C.

ANALYSIS: Calculated for $C_{13}H_{24}N_2$·2HCl: 57.58%C, 5.95%H, 10.33%N. Found: 57.52%C, 6.25%H, 10.23%N.

EXAMPLE 27

1-(2-Phenylethyl)-1,2,3,4-tetrahydrobenzo[c]-1,5-naphthyridine

A stirred solution of 1-(phenylacetyl)-1,2,3,4-tetrahydrobenzo[c]-1,5-naphthyridine (5.11 g) in sieve dried tetrahydrofuran (300 ml) was treated rapidly with 1M borane in tetrahydrofuran (68 ml). The resultant solution was stirred overnight under a nitrogen atmosphere with exclusion of moisture and thereafer allowed to stand 24 hours. The reaction was quenched by dropwise addition of 10% sodium hydroxide solution (60 ml) and then concentrated to remove the tetrahydrofuran. The oil-aqueous phase mixture was further diluted with water (100 ml) and extracted with dichloromethane (2×200 ml). The combined and dried ($Na_2SO_4$) organic phase was filtered and concentrated to a viscous oil (a borane complex of the product). A solution of the oil in glacial acetic acid (30 ml) was cautiously treated with concentrated hydrochloric acid (15 ml) under nitrogen (vigorous gas evolution noted). After stirring for 1 hour at ambient temperature the solution was decanted over crushed ice (500 ml), diluted with water (200 ml) and basified with 50% sodium hydroxide solution. The mixture was extracted with $CH_2Cl_2$ (2×250 ml) and the combined and dried ($Na_2SO_4$) organic phase was filtered and concentrated to an oil (4.72 g). A TLC analysis (silica gel, ethyl acetate) indicated the oil was a mixture of the desired product and 1,2,3,4-tetrahydrobenzo[c]-1,5-naphthyridine. The mixture was separated by preparative HPLC (silica gel, eluted with ethyl acetate, overlap fractions repurified using new columns) to give 1.92 g of the product as a viscous oil which was combined with a similarly prepared material to give 2.52 g of pure product.

ANALYSIS: Calculated: 83.30%C, 6.99%H. Found: 83.08%C, 7.06%H.

EXAMPLE 28

(±)-1-[(2-Trifluoromethylphenyl)methyl]-5-oxo-2-pyrrolidinecarboxylic acid

A solution of 17.40 g of sodium hydroxide pellets in 275 ml of water was treated with 131 g of (±)-1-[(2-trifluoromethylphenyl)methyl]-5-methoxycarbonyl-2-pyrrolidinone and was heated for four hours with a steam bath. The solution was cooled down to room temperature and extracted with diethyl ether (total volume=1000 ml). The aqueous phase was acidified with 50 ml of concentrated hydrochloric acid and extracted with dichloromethane (total volume=900 ml). The organic phase was dried over anhydrous sodium sulfate and concentrated to a solid. The solid was recrystallized from toluene (800 ml) which afforded 49.8 g of crystals, m.p. 139°–141°.

ANALYSIS: Calculated for $C_{13}H_{12}F_3NO_3$: 54.36%C, 4.21%H, 4.88%N. Found: 54.09%C, 4.38%H, 4.78%N.

EXAMPLE 29

1,10a-Dihydro-7-methylpyrrolo[1,2-b]isoquinoline-3,10[2H,5H]-dione

To a solution of 31.49 g of (±)-1-[(3-methylphenyl)methyl]-5-oxo-2-pyrrolidinonecarboxylic acid in anhydrous dichloromethane (800 ml) was added 17.67 g of thionyl chloride, and the resultant solution was stirred and refluxed with the exclusion of moisture for 5 hours. After standing at ambient temperature overnight, the solution was ice-water chilled (3° C.) and 54.0 g of aluminum chloride was added with vigorous stirring. The mixture was stirred for 1.5 hours with the cooling bath in place and then warmed to ambient temperature, followed by stirring and heating (intermittently) with a steam bath for an additional 3 hours in order to increase the rate of reaction. The reaction was quenched by the addition of ice chips and water. The two phases were separated and the aqueous phase was extracted with dichloromethane (1000 ml total). The combined organic phase was dried over anhydrous sodium sulfate, vacuum filtered, and concentrated to an oil, which was stored under refrigeration overnight.

Purification was accomplished by HPLC (silica gel, eluted with ethyl acetate, flow rate: 150 ml/min). The appropriate fractions were combined and concentrated to give a solid. The solid was recrystallized from ethyl acetate (150 ml) to afford 15.21 g of a solid, m.p. 117°–119.5° C.

ANALYSIS: Calculated for $C_{13}H_{13}NO_2$: 72.52%C, 6.09%H, 6.51%N. Found: 72.26%C, 6.11%H, 6.54%N.

EXAMPLE 30

7,8-Dichloro-1,10a-dihydropyrrolo[1,2-b]isoquinoline-3,10-[2H,5H]-dione

To a solution of 20.05 g of (±)-1-[(3,4-dichlorophenyl)methyl]-5-oxo-2-pyrrolidine carboxylic acid in anhydrous dichloromethane (500 ml), 5.6 ml of thionyl chloride was added, and the resultant solution was stirred and refluxed with exclusion of moisture overnight.

An IR spectrum of the solution indicated the presence of the acid chloride. The soluton was ice-water chilled while 27.84 g of aluminum chloride was added in small portions. The mixture was stirred at ambient temperature for 4.5 hours. The reaction was quenched by the addition of ice chips and water. The two phases of the mixture were separated and the aqueous phase was extracted with dichloromethane (450 ml, total volume). The organic phase was dried over anhydrous sodium sulfate and concentrated to a solid which was stored under refrigeration overnight.

The solid was purified by HPLC (silica gel, eluted with ethyl acetate, flow rate: 150 ml/min.) to give 14 g of a solid. This solid was recrystallized from ethyl acetate (350 ml) to afford 8.37 g of a solid, m.p. 189°–192° C.

ANALYSIS: Calculated for $C_{12}H_9Cl_2NO_2$: 53.36%C, 3.36%H, 5.19%N. Found: 53.16%C, 3.52%H, 5.12%N.

EXAMPLE 31

8-Bromo-1,10a-dihydropyrrolo[1,2-b]isoquinoline-3,10-[2H,5H]-dione oxime

A suspension of 88.31 g of 8-bromo-1,10a-dihydropyrrolo[1,2-b]isoquinoline-3,10[2H,5H]-dione in 95% ethanol (550 ml) was treated with a premixed solution of 85.73 g of sodium acetate trihydrate in water (300 ml) and 43.78 g of hydroxylamine hydrochloride in water (300 ml). The solution was refluxed for 2 hours. The reaction mixture was then cooled to room temperature at which time a precipitate began to separate from the mixture. The precipitate was isolated by vacuum filtration.

The solid was recrystallized from 95% ethanol (1800 ml) which afforded 28.37 g of crystals, m.p. 241°–242° C.

ANALYSIS: Calculated for $C_{12}H_{11}BrN_2O_2$: 48.83%C, 3.76%H, 9.49%N. Found: 48.70%C, 3.91%H, 9.37%N.

EXAMPLE 32

7,8-Dichloro-1,10a-dihydropyrrolo[1,2-b]isoquinoline-3,10[2H,5H]-dione oxime

A stirred suspension of 6.37 g of 7,8-dichloro-1,10a-dihydropyrrolo[1,2-b]isoquinoline-3,10[2H,5H]-dione in 95% ethanol (40 ml) was treated with a premixed solution of 3.28 g of hydroxylamine hydrochloride in water (25 ml) and 6.42 g of sodium acetate trihydrate in water (25 ml). The solution was heated at reflux for 2.5 hours. The solution was then cooled with an ice-water bath as a precipitate began to separate from the reaction mixture. The solid was collected by vacuum filtration and recrystallized from 95% ethanol (250 ml) to afford 5.29 g of crystals, m.p. 245°–246° C.

ANALYSIS: Calculated for $C_{12}H_{10}Cl_2N_2O_2$: 50.55%C, 3.54%H, 9.83%N. Found: 50.57%C, 3.45%H, 9.74%N.

EXAMPLE 33

1,4-Dihydro-8-fluorobenzo[c]-1,5-naphthyridin-2(3H)-one

To 55 g of vigorously stirred polyphosphoric acid, which was heated to 105° C., 5.20 g of 1,10a-dihydro-7-fluoropyrrolo[1,2-b]isoquinoline-3,10[2H,5H]-dione oxime was added. After the addition, the mixture turned yellow and the temperature rose to 150° C. The temperature subsided to 105° C. after stirring for 0.5 hour. The reaction was quenched by pouring the mixture into water (2400 ml) and basifying it (pH=10) with a 50% sodium hydroxide solution. A small amount of precipitate was noted. The aqueous mixture was filtered through a coarse sintered glass funnel and the filter cake was collected. The filtrate was extracted with dichloromethane (total volume 4000 ml), dried over anhydrous sodium sulfate, and concentrated to a solid which was combined with the filter cake (2.64 g combined weight). A TLC (thin layer chromatograph) aliquot (silica gel, ethyl acetate) indicated the material was relatively pure. The solid was recrystallized from absolute ethanol (450 ml) to afford 2.12 g of crystals, m.p. 266°–267° C.

ANALYSIS: Calculated for $C_{12}H_9FN_2O$: 66.64%C, 4.20%H, 12.97%N, Found: 66.64%C, 4.27%H, 13.01%N.

EXAMPLE 34

9-Bromo-1,4-dihydrobenzo[c]-1,5-naphthyridin-2(3H)-one

To 300 g of vigorously stirred polyphosphoric acid, which was heated to 110° C., 26.37 g of 8-bromo-1,10a-dihydropyrrolo[1,2-b]isoquinoline-3,10[2H,5H]-dione oxime was added. Upon addition of the oxime, the internal temperature of the mixture rose to 170° C. The mixture was stirred until the internal temperature subsided to approximately 110° C. The reaction was quenched by pouring the mixture into water (3000 ml) and basifying it with 50% sodium hydroxide solution (pH>10). A precipitate separated from the mixture and was collected by vacuum filtraton through a coarse sintered glass funnel.

The solid was recrystallized from 1-propanol (3000 ml) to afford 15.54 g of a solid. A 5.82 g sample was recrystallized from 1-propanol (1400 ml) which afforded 4.29 g of a solid, m.p. 300°–302° C.

ANALYSIS: Calculated for $C_{12}H_9BrN_2O$: 52.01%C, 3.27%H, 10.11%N. Found: 51.83%C, 3.38%H, 10 12%N.

EXAMPLE 35

8,9-Dichloro-1,4-dihydrobenzo[c]-1,5-naphthyridin-2(3H)-one

To 300 g of vigorously stirred polyphosphoric acid, which was heated to 100° C., 21.26 g of 8,9-dichloro-1,10a-dihydropyrrolo[1,2-b]isoquinoline-3,10[2H,5H]- dione oxime was added. The reaction was very exothermic. The mixture was stirred until the internal temperature subsided to 100° C. The reaction was quenched by pouring the mixture into water (3000 ml) and basifying it with a 50% sodium hydroxide solution (pH=10). A precipitate separated from the mixture and was collected by vacuum filtration through a coarse sintered glass funnel. The solid was recrystallized from 1-propanol (800 ml) to afford 12.00 g of crystals, m.p. 350° C.

ANALYSIS: Calculated for $C_{12}H_8Cl_2N_2O$: 53.96%C, 3.02%H, 10.49%N. Found: 53.85%C, 2.92%H, 10.34%N.

EXAMPLE 36

1,4-Dihydro-8-methylbenzo[c]-1,5-naphthyridin-2(3H)-one

To 40 ml of vigorously stirred polyphosphoric acid, which was heated to 100° C., 3.74 g of 1,10a-dihydro-7-methylpyrrolo[1,2-b]isoquinoline-3,10[2H,5H]-dione oxime was added. Upon addition of the oxime, there was a significant exothermic reaction (internal temperature=130° C.). When the temperature subsided to 105° C., the reaction was quenched by pouring the mixture into water (1400 ml) and basifying it with a 50% solution of sodium hydroxide. A precipitate separated from the mixture and was collected by vacuum filtration. The filter cake was dried under vacuum at 65° C. for 3 hours in order to remove any water that was present. The filtrate was extracted with dichloromethane (2000 ml total volume), dried over anhydrous sodium sulfate and concentrated to afford a solid. The combined filter cake and the solid were recrystallized from 1-propanol (100 ml) to afford 2.20 g of a solid, m.p. 265°–266° C.

ANALYSIS: Calculated for $C_{13}H_{12}N_2O$: 73.54%C, 5.70%H, 13.21%N. Found: 73.62%C, 5.89%H, 13.24%N.

EXAMPLE 37

1,4-Dihydro-9-methoxybenzo[c]-1,5-naphthyridin-2(3H)-one

To 110 g of vigorously stirred polyphosphoric acid, which was heated to 100° C., 10.84 g of 1,10a-dihydro-8-methoxypyrrolo[1,2-b]isoquinoline-3,10[2H,5H]-dione oxime was added. Upon addition of the oxime, there was a significant exothermic reaction (internal temperature=140° C.). When the temperature subsided to 100° C., the reaction was quenched by pouring the mixture into water (2400 ml). The mixture was basified with a 50% sodium hydroxide solution which resulted in the formation of a precipitate. The solid (8 g) was collected by vacuum filtration, washed with water (1500 ml) and dried at 60° C. under vacuum for 3 hours in order to remove the water.

A TLC (silica gel, ethyl acetate) showed the solid to be relatively pure. The solid was recrystallized from 1-propanol (500 ml) to afford 5.43 g of crystals, mp 254°–256° C.

ANALYSIS: Calculated for $C_{13}H_{12}N_2O_2$: 68.39%C, 5.30%H, 12.28%N. Found: 68.48%C, 5.42%H, 12.35%N.

EXAMPLE 38

9-Bromo-1,2,3,4-tetrahydrobenzo[c]-1,5-naphthyridine

To a stirred suspension of 4.00 g of 9-bromo-1,4-dihydrobenzo[c]-1,5-naphthyridin-2(3H)-one in tetrahydrofuran (800 ml), 58 ml of borane (1.0M in tetrahydrofuran) was added over approximately one minute. A solution formed after most of the borane was added. The slightly turbid solution was stirred overnight at ambient temperature.

The reaction was quenched by gradual addition of 10% sodium hydroxide solution (150 ml). Gas evolution was noted. The mixture was stirred for 0.5 hour and concentrated with rotary evaporator to remove the tetrahydrofuran which afforded a suspension of solid. The solid was collected by vacuum filtration and suspended in glacial acetic acid (55 ml), and concentrated hydrochloric acid (50 ml) was added dropwise to the suspension with stirring. Gas evolution was noted. The suspension was stirred until a solution formed (~2 hours), decanted into an ice-water mixture (1200 ml) and basified with a 50% sodium hydroxide solution. The aqueous mixture was extracted with dichloromethane (1400 ml total volume), dried over anhydrous sodium sulfate, vacuum filtered and concentrated to a solid. The solid was recrystallized from acetonitrile (100 ml) to afford 2.35 g of crystals, m.p. 181°–183° C.

ANALYSIS: Calculated for $C_{12}H_{11}BrN_2$: 54.77%C, 4.21%H, 10.65%N. Found: 54.40%C, 4.44%H, 10.77%N.

EXAMPLE 39

8-Methyl-1,2,3,4-tetrahydrobenzo[c]-1,5-naphthyridine

To a slightly turbid solution of 3.24 g of 1,4-dihydro-8-methylbenzo[c]-1,5-naphthyridin-2(3H)-one in tetrahydrofuran (800 ml), 62.5 ml of borane (0.98M solution in tetrahydrofuran) was added over approximately one minute. A precipitate formed after half of the borane solution was added. The suspension was stirred overnight at ambient temperature.

A slighly turbid solution had formed overnight. The reaction was quenched by the addition of 10% sodium hydroxide solution (150 ml). Gas evolution was noted. The mixture was stirred for 0.5 hour and concentrated to remove the tetrahydrofuran which afforded a suspension of solid. The solid was collected by vacuum filtration and suspended in glacial acetic acid (40 ml), and concentrated hydrochloric acid (40 ml) was added to the suspension with stirring. Gas evolution was noted. The suspension was stirred until a solution formed (approximately 2 hours). The solution was decanted into an ice-water mixture (1200 ml total volume) and basified with a 50% sodium hydroxide solution. The aqueous mixture was extracted with dichloromethane (1600 ml total volume) and the organic phase was dried over anhydrous sodium sulfate, vacuum filtered and concentrated to afford a solid (4.5 g). The solid was recrystallized from acetonitrile (75 ml) to afford 2.12 g of crystals, m.p. 151°–153.5° C.

ANALYSIS: Calculated for $C_{13}H_{14}N_2$: 78.75%C, 7.12%H. Found: 78.70%C, 7.07%H.

EXAMPLE 40

9-Methoxy-1,2,3,4-tetrahydrobenzo[c]-1,5-naphthyridine

To a slightly turbid solution of 3.88 g of 1,4-dihydro-9-methoxybenzo[c]-1,5-naphthyridin-2(3H)-one in tetrahydrofuran (800 ml), 70 ml of borane (0.98M in tetrahydrofuran) was added over approximately one minute. A precipitate formed almost immediately. The suspension was stirred overnight at ambient temperature.

A solution had formed overnight. The reaction was quenched by the addition of 10% sodium hydroxide solution (120 ml). Gas evolution was noted. The mixture was stirred for 0.5 hour and concentrated to remove the tetrahydrofuran which resulted in a suspension. The solid was collected by vacuum filtration and suspended in glacial acetic acid (40 ml), and concentrated hydrochloric acid (40 ml) was added to the suspension with stirring. Gas evolution was noted. The suspension was stirred until a solution formed (approximately 2 hours) and then decanted into an ice-water mixture (1200 ml total volume) and basified with a 50% solution of sodium hydroxide. The aqueous mixture was extracted with dichloromethane (1500 ml total volume), dried over anhydrous sodium sulfate, vacuum filtered and concentrated to a solid (5 g). The solid was recrystallized from acetonitrile (25 ml) to afford 2.21 g of crystals, m.p. 116°–118.5° C.

ANALYSIS: Calculated for $C_{13}H_{14}N_2O$: 72.85%C, 6.59%H, 13.09%N. Found: 73.09%C, 6.74%H, 13.04%N.

EXAMPLE 41

8,9-Dichloro-1,2,3,4-tetrahydrobenzo[c]-1,5-naphthyridine

To a stirred solution of 4.00 g of 8,9-dichloro-1,4-dihydrobenzo[c]-1,5-naphthyridin-2(3H)-one in tetrahydrofuran (800 ml) was added 60 ml of borane solution (1.0M in tetrahydrofuran) over approximately one minute. A solution formed after the borane addition was complete. The solution was stirred overnight at ambient temperature.

The reaction was quenched by the addition of 10% sodium hydroxide solution (150 ml). Gas evolution was noted. The mixture was stirred for 0.5 hour and concentrated with a rotary evaporator to remove the tetrahydrofuran which afforded a suspension of solid. The solid was collected by vacuum filtration and suspended in glacial acetic acid (60 ml), and concentrated hydrochloric acid (50 ml) was added dropwise to the suspension with stirring. Gas evolution was noted. The suspension was stirred until a solution formed (~2 hours), decanted into an ice-water mixture (1200 ml) and basified with a 50% sodium hydroxide solution. The aqueous mixture was extracted with dichloromethane (1500 ml total volume), dried over anhydrous sodium sulfate, vacuum filtered and concentrated to a solid. The solid was recrystallized twice from acetonitrile (1600 ml, 800 ml) to afford 2.26 g of crystals, m.p. 248°–251° C.

ANALYSIS: Calculated for $C_{12}H_{10}Cl_2N_2$: 56.94%C, 3.98%H, 11.07%N. Found: 56.48%C, 3.90%H, 11.02%N.

EXAMPLE 42

1-(2-Bromopropionyl)-1,2,3,4-tetrahydrobenzo[c]-1,5-naphthyridine hydrobromide

A solution of 15.0 g of 1,2,3,4-tetrahydrobenzo[c]-1,5-naphthyridine in 24 ml of 2-bromopropionyl bromide was stirred overnight at ambient temperature. The solution was then diluted with anhydrous diethyl ether and stirred for approximately 3 hours at ambient temperature. A precipitate separated from the solution. The precipitate was collected by vacuum filtration and dried under vacuum at 40° C. overnight. The solid was recrystallized from a mixture of 95% ethanol and anhydrous diethyl ether (1:2) to yield 28.22 g of a powdery solid.

ANALYSIS: Calculated for $C_{15}H_{15}BrN_2O \cdot HBr$: 45.04%C, 4.03%H, 7.01%N. Found: 44.79%C, 4.02%H, 6.98%N.

EXAMPLE 43

1-(2-Aminopropionyl)-1,2,3,4-tetrahydrobenzo[c]-1,5-naphthyridine

A solution of 4.86 g of 1-(2-bromopropionyl)-1,2,3,4-tetrahydrobenzo[c]-1,5-naphthyridine in methanol (300 ml) was cooled to 0° C. Anhydrous ammonia was then bubbled through the chilled solution for 3 hours, after which time the solution was allowed to equilibrate to ambient temperature and stirred overnight. The solution was concentrated and the resultant solid was dissolved in dichloromethane. The organic phase was extracted with 10% hydrochloric acid. The aqueous phase was then basified with sodium hydroxide and extracted with dichloromethane. The organic phase was dried, vacuum filtered, and concentrated to a viscous oil.

Partial purification was accomplished by HPLC (silica gel, eluted with methanol, flow rate: 200 ml/min). The appropriate fractions were combined and concentrated to give a solid. This material was combined with another batch of sample and recrystallized from toluene (20 ml) to yield crystals, m.p. 97°–101° C.

ANALYSIS: Calculated for $C_{15}H_{17}N_3O$: 70.56%C, 6.71%H, 16.46%N. Found: 70.30%C, 6.67%H, 16.22%N.

EXAMPLE 44

1-[(2-Fluorophenyl)acetyl]-1,2,3,4-tetrahydrobenzo[c]-1,5-naphthyridine

Ice cold freshly distilled 2-fluorophenylacetylchloride (39 ml) was treated with powdered 1,2,3,4-tetrahydrobenzo[c]-1,5-naphthyridine (7.94 g) under good stirring without external cooling. The reaction was mildly exothermic and a suspension formed with a few minutes. After stirring overnight at ambient temperature, the suspension was diluted with anhydrous ether and stirred for 1.5 hours. The material was isolated by vacuum filtration, washed thoroughly with ether and dissolved in water (20 ml) to give a cloudy solution. The solution was basified with 2.5N sodium hydroxide and extracted with dichloromethane (2×250 ml). The dried (anhydrous sodium sulfate) organic phase was filtered and concentrated to an oil (15.87 g). Thin layer chromatographic analysis (silica, ethyl acetate) indicated a multi-component mixture in which the desired product ($R_f$=0.28) and the starting amine predominated. The mixture was separated by HPLC (silica gel, sample applied in 30 ml of dichloromethane, eluted with ethyl acetate, 200 ml/min. flow rate, recycled once to optimize separation) to give 9.72 g of the product as an oil. Trituration of the oil with anhydrous ether gave 8.54 g of the product as a solid, m.p. 114°–115.5° C.

ANALYSIS: Calculated for $C_{20}H_{17}FN_2O$: 74.98%C, 5.35%H, 8.74%N. Found: 74.91%C, 5.56%H, 8.66%N.

EXAMPLE 45

1-[(2-Chlorophenyl)acetyl]-1,2,3,4-tetrahydrobenzo[c]-1,5-naphthyridine

Powdered 1,2,3,4-tetrahydrobenzo[c]-1,5-naphthyridine (8.29 g) was added to ice cold, stirred 2-chlorophenylacetyl chloride (30 ml) without external cooling. A thick suspension of crystalline material formed and a mild exothermic reaction was observed. After stirring overnight at room temperature the suspension was gradually diluted with anhydrous ether to give a tacky solid which formed a gummy mass. On continued stirring the material solidified and disintegrated to give a suspension. The material was isolated by vacuum filtration and washed well with ether. A solution of the filter cake and water (300 ml) was basified with 10% sodium hydroxide solution and extracted with dichloromethane (2×250 ml). The combined turbid organic phase was washed once with saturated brine, dried over anhydrous sodium sulfate, filtered and concentrated to an oil. A solution of the oil and toluene (150 ml) was concentrated to remove any residual moisture, whereupon the material solidified. Thin layer chromatographic analysis (silica gel, ethyl acetate) indicated the presence of 40–50% starting material. A solution of the solid in dichloromethane (200 ml) was added to stirred, ice-cold 2-chlorophenylacetyl chloride (27 ml) without external cooling. After three hours, the solution was concentrated to reduce the reaction volume, whereupon a suspension formed. Sufficient dichloromethane (200 ml) was added to afford a solution which was allowed to stand for 48 hours at room temperature. The solution was concentrated to remove most of the dichloromethane and the residual oil was treated with excess ethereal hydrogen chloride and diluted with ether (400 ml) to give a tacky precipitate. The ether was decanted and the precipitate was triturated with fresh ether (solidified). The solid was isolated by vacuum filtration, washed well with ether and converted to the free base. Thin layer chromatographic analysis (silica gel, ethyl acetate) indicated the presence of a small amount of starting amine, the product and two higher $R_f$ spots. The mixture was separated by HPLC (silica gel; sample applied in 200 ml of dichloromethane; eluted with ethyl acetate; 200 ml/min flow rate; recycle technique utilized to optimize the separation). The appropriate fractions were combined and concentrated to give a solid (7.97 g) which was triturated with ether, filtered, and dried in vacuo at 40° C., m.p. 176°–178° C.

ANALYSIS: Calculated for $C_{20}H_{17}ClN_2O$: 71.32%C, 5.09%H, 8.32%N. Found: 71.29%C, 5.09%H, 8.42%N.

EXAMPLE 46

1-[(4-Chlorophenyl)acetyl]-1,2,3,4-tetrahydrobenzo[c]-1,5-naphthyridine

To 40 ml of ice-cold 4-chlorophenylacetyl chloride was added 8.11 g of 1,2,3,4-tetrahydrobenzo[c]-1,5-naphthyridine. The suspension was stirred overnight at ambient temperature. Anhydrous diethyl ether was added and the suspension was stirred for 2 hours. The solid was collected by vacuum filtration, dissolved in water (175 ml), and basified with 50% sodium hydroxide solution. The aqueous mixture was extracted with dichloromethane (300 ml) and the organic phase was dried over anhydrous sodium sulfate, vacuum filtered, and concentrated to an oil.

Purification was accomplished by HPLC (silica gel, eluted with ethyl acetate, flow rate: 150 ml/min). The appropriate fractions were combined and concentrated to an oil. The oil was triturated with anhydrous ether to yield 11.54 g of crystals, m.p. 114°–116° C.

ANALYSIS: Calculated for $C_{20}H_{17}ClN_2O$: 71.32%C, 5.09%H, 8.32%N. Found: 70.92%C, 5.29%H, 8.15%N.

EXAMPLE 47

1-[(2-Methoxyphenyl)acetyl]-1,2,3,4-tetrahydrobenzo[c]-1,5-naphthyridine

To 35 ml of ice-cold 2-methoxyphenylacetyl chloride was added 8.10 g of 1,2,3,4-tetrahydrobenzo[c]-1,5-naphthyridine. The suspension was stirred overnight at ambient temperature. Anhydrous diethyl ether was added and the suspension was stirred for 2 hours. The solid was collected by vacuum filtration, dissolved in water and basified with 50% sodium hydroxide solution. The aqueous mixture was extracted with dichloromethane (500 ml, total) and dried over anhydrous sodium sulfate, and the organic phase was vacuum filtered and concentrated to an oil.

Purification was accomplished by HPLC (silica gel, eluted with ethyl acetate, flow rate: 150 ml/min). The appropriate fractions were combined and concentrated to an oil. Crystals formed when the oil was triturated with diethyl ether. The material was recrystallized from ethyl acetate (50 ml) to afford 5.40 g of crystals, m.p. 108°–111° C.

ANALYSIS: Calculated for $C_{21}H_{20}N_2O_2$: 75.88%C, 6.06%H, 8.43%N. Found: 75.71%C, 6.11%H, 8.63%N.

EXAMPLE 48

1-[(4-Methoxyphenyl)acetyl]-1,2,3,4-tetrahydrobenzo[c]-1,5-naphthyridine

To 40 ml of ice-cold 4-methoxyphenylacetyl chloride, was added 10.0 g of 1,2,3,4-tetrahydrobenzo[c]-1,5-naphthyridine. The suspension was stirred overnight at ambient temperature. The suspension was diluted with anhydrous diethyl ether and stirred for 2 hours. The solid was collected by vacuum filtration, dissolved in water and basified with 50% sodium hydroxide solution. The aqueous mixture was extracted with dichloromethane (700 ml) and the organic phase was dried over anhydrous sodium sulfate, vacuum filtered and concentrated to an oil.

Purification was accomplished by HPLC (silica gel, eluted with ethyl acetate, flow rate: 150 ml/min). The appropriate fractions were combined and concentrated to an oil. Crystals formed when the oil was triturated with diethyl ether, m.p. 69°–71° C.

ANALYSIS: Calculated for $C_{21}H_{20}N_2O_2$: 75.88%C, 6.06%H, 8.43%N. Found: 75.83%C, 6.09%H, 8.37%N.

EXAMPLE 49

1-(2-Thienyl)acetyl-1,2,3,4-tetrahydrobenzo[c]-1,5-napthyridine

To 40 ml of ice-cold 2-thienylacetyl chloride was added 10.00 g of 1,2,3,4-tetrahydrobenzo[c]-1,5-napthyridine. The suspension was stirred overnight at ambient temperature. Anhydrous diethyl ether was added and the suspension was stirred for 3 hours. The solid was collected by vacuum filtration and dissolved in water, and the solution was basified with 50% sodium hydroxide solution. The aqueous mixture was extracted with dichloromethane (700 ml), and the organic phase was dried over anhydrous sodium sulfate, vacuum filtered and concentrated to an oil.

Purification was accomplished by HPLC (silica gel, eluted with ethyl acetate, flow rate: 150 ml/min). The appropriate fractions were combined and concentrated to an oil. The oil was triturated with anhydrous diethyl ether to yield 8.90 g of crystals, m.p. 102°–103° C.

ANALYSIS: Calculated for $C_{18}H_{16}N_2OS$: 70.10%C, 5.23%H, 9.08%N. Found: 70.04%C, 5.34%H, 9.00%N.

EXAMPLE 50

1-(3-Thienyl)acetyl-1,2,3,4-tetrahydrobenzo[c]-1,5-naphthyridine

To 35 ml of ice-cold 3-thienylacetyl chloride was added 8.12 g of 1,2,3,4-tetrahydrobenzo[c]-1,5-naphthyridine. The suspension was stirred overnight at ambient temperature. Anhydrous ether was added and the suspension was stirred for an additional 3 hours. The solid was collected by vacuum filtration and dissolved in water, and the solution was basified with 50% sodium hydroxide solution. The aqueous mixture was extracted with dichloromethane (800 ml), and the organic phase was dried over anhydrous sodium sulfate, vacuum filtered and concentrated to an oil.

Purification was accomplished by HPLC (silica gel, eluted with ethyl acetate, flow rate: 150 ml/min). The appropriate fractions were combined and concentrated to an oil. The oil was triturated with anhydrous diethyl ether to yield 7.56 g of crystals, m.p. 97°–99° C.

ANALYSIS: Calculated for $C_{18}H_{16}N_2OS$: 70.10%C, 5.23%H, 9.08%N. Found: 69.98%C, 5.44%H, 8.99%N.

EXAMPLE 51

1-[3-(Phenyl)propyl]-1,2,3,4-tetrahydrobenzo[c]-1,5-naphthyridine dihydrochloride A stirred solution of 1-[(1-oxo-3-phenyl)propyl]-1,2,3,4-tetrahydrobenzo[c]-1,5-naphthyridine (8.64 g) in anhydrous tetrahydrofuran (700 ml) was rapidly treated with 1.0M borane solution in tetrahydrofuran (110 ml, 0.11 mole of $BH_3$). After stirring overnight at room temperature with exclusion of moisture, 2.5N sodium hydroxide solution (110 ml) was added dropwise under nitrogen purge (vigorous gas evolution noted). The mixture was then concentrated to remove the tetrahydrofuran and the residual oil-aqueous phase was extracted with dichloromethane (3×250 ml). The organic phase was dried over anhydrous sodium sulfate, filtered and concentrated to an oil, which was dissolved in glacial acetic acid (80 ml). After stirring for approximately 20 minutes, a suspension of solid formed. The suspension was treated in portions with concentrated hydrochloric acid (10 ml, vigorous gas evolution noted) to give a clear solution. On continued stirring, a suspension of solid formed. The mixture was decanted over crushed ice (500 ml), diluted with water and basified with 50% sodium hydroxide solution. The turbid mixture was extracted with dichloromethane (3×150 ml) and the combined organic phase was dried over anhydrous sodium sulfate, filtered and concentrated to an oil (8.34 g). Thin layer chromatographic analysis (silica gel, ethyl acetate) indicated the oil was mainly a mixture of the desired product and 1,2,3,4-tetrahydrobenzo[c]-1,5-naphthyridine. The mixture was separated by preparative HPLC runs (silica gel, sample applied in dichloromethane, eluted with ethyl acetate, 200 ml/min. flow rate). Concentration of the appropriate fractions gave 3.53 g of the product as an oil. A solution of the oil in methanol (25 ml) was treated with excess ethereal hydrogen chloride. The thick suspension was diluted with methanol (20 ml) to facilitate stirring and further diluted with anhydrous ether (200 ml). The suspension was vacuum filtered and the filter cake was washed twice with ether. A warm solution of the filter cake in methanol (100 ml) was gradually diluted with ether in 25 ml increments to give a total volume of 500 ml. The precipitate was isolated, washed with anhydrous ether and dried in vacuo at 40° C. to give 3.02 g of a solid (light sensitive), m.p. 198°–202.5° C.

ANALYSIS: Calculated for $C_{21}H_{22}N_2.2HCl$: 67.20%C, 6.44%H, 7.46%N. Found: 66.93%C, 6.36%H, 7.48%N.

EXAMPLE 52

1-[2-(2-Fluorophenyl)ethyl]-1,2,3,4-tetrahydrobenzo[c]-1,5-naphthyridine hydrochloride A stirred solution of 1-[(2-fluorophenyl)acetyl]-1,2,3,4-tetrahydrobenzo[c]-1,5-naphthyridine (6.1 g) in tetrahydrofuran (500 ml) was treated rapidly with 1M borane solution in tetrahydrofuran (76 ml, 0.076 mole of $BH_3$). A yellow color developed within a few minutes and the solution was stirred overnight at room temperature with exclusion of moisture. The reaction was quenched by dropwise addition of 2.5N sodium hydroxide solution (100 ml, vigorous gas evolution observed) and the reaction mixture was concentrated to remove the tetrahydrofuran. The residual aqueous phase-oil phase mixture was extracted with dichloromethane (2×150 ml), and the combined organic phase was dried over anhydrous sodium sulfate, filtered and concentrated to an oil. A stirred solution of the oil in glacial acetic acid (70 ml) was gradually treated with concentrated hydrochloric acid (20 ml) under nitrogen (gas evolution observed). After stirring 3 hours at room temperature, the solution was decanted over crushed ice (400 ml), diluted with water (300 ml) and basified with 50% sodium hydroxide solution.

The turbid mixture was extracted with dichloromethane (2×200 ml) and the combined organic phase was dried over anhydrous sodium sulfate, filtered and concentrated to an oil (5.85 g). Thin layer chromatographic analysis (silica gel, ethyl acetate) indicated a mixture (4 components). The oil was purified by preparative HPLC (silica gel; sample applied in dichloromethane; eluted with ethyl acetate; 200 ml/min flow rate) to afford the product (3.12 g) as a clear oil. A solution of the oil in methanol (15 ml) was treated with excess ethereal hydrogen chloride (8 ml) and the resultant solution was gradually diluted with anhydrous ether almost to the cloud point. Seeding with crystals obtained from a trial preparation of the salt and further dilution with ether gave 1.92 g of crystals, m.p. 216.5°–222° C.

ANALYSIS: Calculated for $C_{20}H_{19}FN_2.HCl$: 70.07%C, 5.88%H, 8.17%N. Found: 69.48%C, 5.96%H, 8.03%N.

EXAMPLE 53

1-[2-(2-Chlorophenyl)ethyl]-1,2,3,4-tetrahydrobenzo[c]-1,5-naphthyridine hydrochloride A stirred colorless solution of 1-[(2-chlorophenyl)acetyl]-1,2,3,4-tetrahydrobenzo[c]-1,5-naphthyridine (5.7 g) in tetrahydrofuran (500 ml) was treated rapidly with 1M borane solution in tetrahydrofuran (68 ml, 0.068 mole of $BH_3$, 4-fold excess) under nitrogen. A yellow color appeared within one minute. After stirring overnight at room temperature with exclusion of moisture, the reaction was quenched by dropwise addition of 10% sodium hydroxide solution (100 ml, gas evolution). The mixture was concentrated to remove the tetrahydrofuran and the aqueous residue was extracted with dichloromethane (2×250 ml). The combined organic phase was dried over anhydrous sodium sulfate, filtered and concentrated to give a viscous gum (borane complex) which was dissolved in glacial acetic acid and treated portion-wise with concentrated hydrochloric acid (25 ml, gas evolution). The resultant solution was stirred for 3 hours at ambient temperature, decanted into ice water (500 ml), basified with 50% sodium hydroxide solution and extracted with dichloromethane (2×250 ml). The organic phase was dried over anhydrous sodium sulfate, filtered and concentrated to an oil (5.43 g). Thin layer chromatographic analysis (silica gel, ethyl acetate) indicated a mixture. The material was purified by HPLC (silica gel, sample applied in 25 ml of dichloromethane, eluted with ethyl acetate, 200 ml/min flow rate), and the appropriate fractions were combined and concentrated to an oil (2.90 g). A solution of the oil in methanol (10 ml) was treated with a slight excess of ethereal hydrogen chloride, followed by dilution with anhydrous ether almost to the cloud point. The solution was seeded with a material obtained from a small scale recrystallization, whereupon crystals precipitated rapidly. After standing 20 minutes (exclusion of light), the precipitate was isolated by vacuum filtration, washed thoroughly with ether and dried in vacuo at 40° C. to give 2.51 g of crystals, m.p. 218°–220° C.

ANALYSIS: Calculated for $C_{20}H_{19}ClN_2 \cdot HCl$: 66.86%C, 5.61%H, 7.80%N. Found: 66.89%C, 5.72%H, 7.75%N.

EXAMPLE 54

1-[2-(4-Chlorophenyl)ethyl]-1,2,3,4-tetrahydrobenzo[c]-1,5-naphthyridine hydrochloride A solution of 3.54 g of 1-[(4-chlorophenyl)acetyl]-1,2,3,4-tetrahydrobenzo[c]-1,5-naphthyridine in tetrahydrofuran (250 ml) was treated with one portion of 1M borane solution in tetrahydrofuran (42 ml). The mixture was stirred overnight at ambient temperature.

The reaction was quenched by the gradual addition of 10% sodium hydroxide solution (150 ml). Gas evolution was noted. The mixture was stirred for 0.5 hour and concentrated to remove the tetrahydrofuran. The aqueous phase was extracted with dichloromethane (300 ml). The organic phase was dried over anhydrous sodium sulfate, vacuum filtered and concentrated to an oil. The oil was placed in glacial acetic acid and treated dropwise with concentrated hydrochloric acid. Gas evolutoin was note. The mixture was stirred at ambient temperature until a solution formed (~3 hours), decanted into an ice-water mixture and basified with 50% sodium hydroxide solution. The aqueous phase was extracted with dichloromethane (700 ml) and the organic phase was dried over anhydrous sodium sulfate, vacuum filtered and concentrated to an oil which was stored under refrigeration overnight.

Purification was accomplished by HPLC (silica gel, eluted with ethyl acetate, flow rate: 150 ml/min). The appropriate fractions were combined and concentrated to an oil. This oil and an oil from a previous run of same reaction were combined, added to methanol (10 ml) and treated with ethereal hydrogen chloride. The solution was diluted with diethyl ether, whereupon crystals began to precipitate. The crystals were collected by vacuum filtration (2.1 g), m.p. 191°–195° C.

ANALYSIS: Calculated for $C_{20}H_{19}ClN_2 \cdot HCl$: 66.82%C, 5.61%H, 7.80%N. Found: 66.97%C, 5.87%H, 7.78%N.

EXAMPLE 55

1-[2-(2-Methoxyphenyl)ethyl]-1,2,3,4-tetrahydrobenzo[c]-1,5-naphthyridine hydrochloride hemihydrate A solution of 10.53 g of 1-[(2-methoxyphenyl)acetyl]-1,2,3,4-tetrahydrobenzo[c]-1,5-naphthyridine in tetrahydrofuran (600 ml) was treated with one portion of 1M borane solution in tetrahydrofuran (127 ml, 0.127 mole of borane). The solution was stirred overnight at ambient temperature.

The reaction was quenched by the gradual addition of 10% sodium hydroxide solution (125 ml). Gas evolution was noted. The mixture was stirred for 0.5 hour and concentrated to remove the tetrahydrofuran. The aqueous phase was extracted with dichloromethane (550 ml total), and the organic phase was dried over anhydrous sodium sulfate, vacuum filtered and concentrated to an oil. The oil was placed in glacial acetic acid (200 ml) and treated dropwise with concentrated hydrochloric acid (60 ml). Gas evolution was noted. The mixture was stirred at ambient temperature until a solution formed (3 hours). The mixture was then decanted into ice-water and basified with 50% sodium hydroxide solution. The aqueous phase was extracted with dichloromethane (700 ml) and the organic phase was dried over anhydrous sodium sulfate, vacuum filtered and concentrated to an oil which was stored under refrigeration overnight.

Purification was accomplished by HPLC (silica gel, eluted with ethyl acetate, flow rate 150 ml/min). The appropriate fractions were combined and concentrated to an oil. The oil was dissolved in methanol and treated with ethereal hydrogen chloride. The solution was diluted with anhydrous diethyl ether, whereupon crystals precipitated. The crystals were collected by vacuum filtration and dried at 100° C. in an oven under high vacuum for 7.5 hours to obtain 5.74 g of crystals, m.p. 200°–202° C.

ANALYSIS: Calculated for $C_{21}H_{22}N_2O \cdot HCl \cdot 0.5 H_2O$: 69.30%C, 6.37%H, 7.70%N. Found: 69.61%C, 6.45%H, 7.69%N.

EXAMPLE 56

1-[2-(4-Methoxyphenyl)ethyl]-1,2,3,4-tetrahydrobenzo[c]-1,5-naphthyridine hydrochloride hemihydrate A solution of 6.28 g of 1-[(4-methoxyphenyl)acetyl]-1,2,3,4-tetrahydrobenzo[c]-1,5-naphthyridine in tetrahydrofuran (500 ml) was treated with one portion of 1M borane solution in tetrahydrofuran (76 ml, 0.076 mole of borane). The solution was stirred overnight at ambient temperature.

The reaction was quenched by the gradual addition of 10% sodium hydroxide solution (85 ml). Gas evolution was noted. The mixture was stirred for 0.5 hour and concentrated to remove the tetrahydrofuran. The aqueous phase was extracted with dichloromethane, and the organic phase was dried over anhydrous sodium sulfate, vacuum filtered and concentrated to an oil. The oil was placed in glacial acetic acid (100 ml) and treated dropwise with concentrated hydrochloric acid (55 ml). Gas evolution was noted. The mixture was stirred at ambient temperature until a solution formed (2.5 hours). The mixture was then decanted into ice-water and basified with 50% sodium hydroxide solution. The aqueous phase was extracted with dichloromethane (1600 ml), and the organic phase was dried over anhydrous sodium sulfate, vacuum filtered and concentrated to an oil which was stored under refrigeration overnight.

Purification was accomplished by HPLC (silica gel, eluted with ethyl acetate, flow rate 150 ml/min). The appropriate fractions were combined and concentrated to an oil. The oil was dissolved in methanol and treated with ethereal hydrogen chloride. The solution was diluted with anhydrous diethyl ether, whereupon crystals precipitated. The crystals were collected by vacuum filtration and dried overnight at 60° C. under high vacuum to obtain 2.39 g of crystals, m.p. 180°–182° C.

ANALYSIS: Calculated for $C_{21}H_{22}N_2O \cdot HCl \cdot 0.5 H_2O$: 69.30%C, 6.65%H, 7.70%N. Found: 69.71%C, 6.45%H, 7.69%N.

EXAMPLE 57

1-[2-(2-Thienyl)ethyl]-1,2,3,4-tetrahydrobenzo[c]-1,5-naphthyridine hydrochloride A solution of 7.40 g of 1-[(2-thienyl)acetyl]-1,2,3,4-tetrahydrobenzo[c]-1,5-naphthyridine in tetrahydrofuran (650 ml) was treated with one portion of 1M borane solution in tetrahydrofuran (96 ml, 0.096 mole of borane). The solution was stirred overnight at ambient temperature. The reaction was quenched by the gradual addition of 10% sodium hydroxide solution (125 ml). Gas evolution was noted. The mixture was stirred for 0.5 hour and concentrated to remove the tetrahydrofruan. The aqueous phase was extracted with dichloroemthane (400 ml), and the organic phase was dried over anhydrous sodium sulfate, vacuum filtered and concentrated to a gum. The gum was dissolved in glacial acetic acid (150 ml) and treated dropwise with concentrated hydrochloric acid (60 ml). Gas evolution was noted. The mixture was then decanted into ice-water and basified with 50% sodium hydroxide solution. The aqueous mixture was extracted with dichloromethane (500 ml), and the organic phase was dried over anhydrous sodium sulfate, vacuum filtered and concentrated to an oil which was stored under refrigeration overnight.

Purification was accomplished by HPLC (silica gel, eluted with ethyl acetate, flow rate 150 ml/min). The appropriate fractions were combined and concentrated to an oil. The oil was dissolved in methanol (25 ml) and treated with ethereal hydrogen chloride. The solution was diluted with anhydrous diethyl ether, whereupon crystals precipitated. The crystals were collected by vacuum filtration and dried overnight under vacuum at 65° C. to obtain 2.96 g of crystals., m.p. 191°–195° C.

ANALYSIS: Calculated for $C_{18}H_{18}N_2S \cdot HCl$: 65.32%C, 5.79%H, 8.47%N. Found: 65.02%C, 5.93%H, 8.44%N.

EXAMPLE 58

1-[2-(3-Thienyl)ethyl]-1,2,3,4-tetrahydrobenzo[c]-1,5-naphthyridine hydrochloride A solution of 5.56 g of 1-(3-thienyl)acetyl-1,2,3,4-tetrahydrobenzo[c]-1,5-naphthyridine in tetrahydrofuran (500 ml) was treated with one portion of 1M borane solution in tetrahydrofuran (73 ml, 0.073 mole of borane). The solution was stirred overnight at ambient temperature.

The reaction was quenched by the gradual addition of 10% sodium hydroxide solution (125 ml). Gas evolution was noted. The mixture was stirred for 0.5 hour and concentrated to remove the tetrahydrofuran. The aqueous phase was extracted with dichloromethane (600 ml), and the organic phase was dried over anhydrous sodium sulfate, vacuum filtered and concentrated to a gum. The gum was dissolved in glacial acetic acid (120 ml) and treated dropwise with concentrated hydrochloric acid (60 ml). Gas evolution was noted. The mixture was stirred at ambient temperature for 3 hours. The mixture was then decanted into ice-water and basified with 50% sodium hydroxide solution. The aqueous phase was extracted with dichloromethane (50 ml) and the organic phase was dried over anhydrous sodium sulfate, vacuum filtered and concentrated to an oil which was stored under refrigeration overnight.

Purification was accomplished by HPLC (silica gel, eluted with ethyl acetate, flow rate 150 ml/min). The appropriate fractions were combined and concentrated to an oil. The oil was dissolved in methanol and treated with ethereal hydrogen chloride. The solution was diluted with anhydrous diethyl ether, whereupon crystals precipitated. The crystals were collected by vacuum filtration and dried overnight at ambient temperature under vacuum to obtain 2.18 g of crystals, m.p. 208°–211° C.

ANALYSIS: Calculated for $C_{18}H_{18}N_2S \cdot HCl$: 65.32%C, 5.79%H, 8.47%N. Found: 65.36%C, 5.83%H, 8.47%N.

We claim:

1. A compound having having the formula

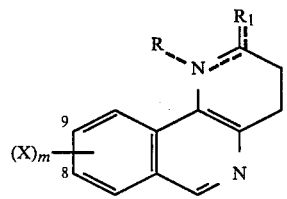

where m is 1 or 2; each X is independently H, halogen, loweralkyl, loweralkoxy, —$CF_3$ or —OH, R is H, loweralkyl, chloroloweralkyl, bromoloweralkyl, iodoloweralkyl, aminoloweralkyl, loweralkylaminoloweralkyl, diloweralkylaminoloweralkyl, arylloweralkyl, diarylloweralkyl, thienylloweralkyl, furylloweralkyl, loweralkanoyl, chloroloweralkanoyl, bromoloweralkanoyl, iodoloweralkanoyl, aminoloweralkanoyl, loweralkylaminoloweralkanoyl, diloweralkylaminoloweralkanoyl, aroyl, arylloweralkanoyl, diarylloweralkanoyl, thienylloweralkanoyl or furylloweralkanoyl; and $R_1$ is =O,

or —$NR_2R_3$, $R_2$ and $R_3$ being independently H or loweralkyl, or taken together with the nitrogen atom to which they are attached constituting

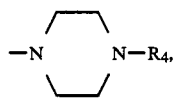

$R_4$ in turn being H, loweralkyl, hydroxyloweralkyl, aryl, arylloweralkyl or diarylloweralkyl, wherein the term aryl in each occurrence means a phenyl group having 0, 1, 2 or 3 substituents each of which being independently loweralkyl, loweralkoxy, halogen or CF₃, except that said substituents may not be three adjacent tertiary butyl groups or iodo groups, with the proviso that when R₁ is —NR₂R₃, R is nonexistent, that when R₁=O, R is not an acyl group and that when R₁ is

is not chloroloweralkyl, bromoloweralkyl or iodoloweralkyl; or a pharmaceutically acceptable acid addition salt thereof.

2. The compound as defined in claim 1 where R₁ is =O.

3. The compound as defined in claim 2, where R is H.

4. The compound as defined in claim 3, where m is 1.

5. The compound as defined in claim 4, where X is H, which is 1,4-dihydrobenzo[c]-1,5-naphthyridin-2(3H)-one.

6. The compound as defined in claim 4, where X is halogen.

7. The compound as defined in claim 6, where X is chlorine.

8. The compound as defined in claim 7, where X is 8-chloro, which is 8-chloro-1,4-dihydrobenzo[c]-1,5-naphthyridin-2(3H)-one.

9. The compound as defined in claim 7, where X is 9-chloro, which is 9-chloro-1,4-dihydrobenzo[c]-1,5-naphthyridin-2(3H)-one.

10. The compound as defined in claim 6, where X is fluorine.

11. The compound as defined in claim 10, where X is 8-fluoro, which is 1,4-dihydro-8-fluorobenzo[c]-1,5-naphthyridin-2(3H)-one.

12. The compound as defined in claim 6, where X is bromine.

13. The compound as defined in claim 12, where X is 9-bromo, which is 9-bromo-1,4-dihydrobenzo[c]-1,5-naphthyridin-2(3H)-one.

14. The compound as defined in claim 4, where X is loweralkoxy.

15. The compound as defined in claim 14, where X is methoxy.

16. The compound as defined in claim 15, where X is 9-methoxy, which is 1,4-dihydro-9-methoxybenzo[c]-1,5-naphthyridin-2(3H)-one.

17. The compound as defined in claim 4, where X is loweralkyl.

18. The compound as defined in claim 17, where X is methyl.

19. The compound as defined in claim 18, where X is 8-methyl, which is 1,4-dihydro-8-methylbenzo[c]-1,5-naphthyridin-2(3H)-one.

20. The compound as defined in claim 3, where m is 2.

21. The compound as defined in claim 20, where both X-groups are chlorine.

22. The compound as defined in claim 21, where the X-groups are 8-chloro and 9-chloro, which is 8,9-dichloro-1,4-dihydrobenzo[c]-1,5-naphthyridin-2(3H)-one.

23. The compound as defined in claim 1, where R₁ is —NR₂R₃.

24. The compound as defined in claim 23, where R₂ is H and R₃ is loweralkyl.

25. The compound as defined in claim 24, where R₃ is methyl.

26. The compound as defined in claim 25, where m is 1 and X is H, which is 3,4-dihydro-2-methylaminobenzo[c]-1,5-naphthyridine.

27. The compound as defined in claim 23, where —NR₂R₃ is

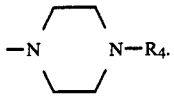

28. The compound as defined in claim 27, where R₄ is methyl.

29. The compound as defined in claim 28, where m is 1 and X is H, which is 3,4-dihydro-2-(4-methyl-1-piperazinyl)benzo[c]-1,5-naphthyridine.

30. The compound as defined in claim 2, where R is arylloweralkyl.

31. The compound ad defined in claim 30, where R is phenylloweralkyl.

32. The compound as defined in claim 31, where R is benzyl.

33. The compound as defined in claim 31, where m is 1 and X is H, which is 1,4-dihydro-1-phenylmethylbenzo[c]-1,5-naphthyridin-2(3H)-one.

34. The compound as defined in claim 1, where R₁ is

35. The compound as defined in claim 34, where R is H.

36. The compound as defined in claim 35, where m is 1.

37. The compound as defined in claim 36, where X is H, which is 1,2,3,4-tetrahydrobenzo[c]-1,5-naphthyridine.

38. The compound as defined in claim 36, where X is halogen.

39. The compound as defined in claim 38, where X is chlorine.

40. The compound as defined in claim 39, where X is 9-chloro, which is 9-chloro-1,2,3,4-tetrahydrobenzo[c]-1,5-naphthyridine.

41. The compound as defined in claim 38, where X is bromine.

42. The compound as defined in claim 41, where X is 9-bromo, which is 9-bromo-1,2,3,4-tetrahydrobenzo[c]-1,5-naphthyridine.

43. The compound as defined in claim 36, where X is loweralkoxy.

44. The compound as defined in claim 43, where X is methoxy.

45. The compound as defined in claim 44, where X is 9-methoxy, which is 9-methoxy-1,2,3,4-tetrahydrobenzo[c]-1,5-naphthyridine.

46. The compound as defined in claim 36, where X is loweralkyl.

47. The compound as defined in claim 46, where X is methyl.

48. The compound as defined in claim 47, where X is 8-methyl, which is 8-methyl-1,2,3,4-tetrahydrobenzo[c]-1,5-naphthyridine.

49. The compound as defined in claim 35, where both X-groups are chlorine.

50. The compound as defined in claim 49, where the X-groups are 8-chloro and 9-chloro, which is 8,9-dichloro-1,2,3,4-tetrahydrobenzo[c]-1,5-naphthyridine.

51. The compound as defined in claim 34, where R is loweralkanoyl.

52. The compound as defined in claim 51, where R is formyl.

53. The compound as defined in claim 52, where m is 1 and X is H, which is 1-formyl-1,2,3,4-tetrahydrobenzo[c]-1,5-naphthyridine.

54. The compound as defined in claim 34, where R is bromoloweralkanoyl.

55. The compound as defined in claim 54, where R is 2-bromopropionyl.

56. The compound as defined in claim 55, where m is 1 and X is H, which is 1-(2-bromopropionyl)-1,2,3,4-tetrahydrobenzo[c]-1,5-naphthyridine.

57. The compound as defined in claim 34, where R is aminoloweralkanoyl.

58. The compound as defined in claim 57, where R is 2-aminopropionyl.

59. The compound as defined in claim 58, where m is 1 and X is H, which is 1-(2-aminopropionyl)-1,2,3,4-tetrahydrobenzo[c]-1,5-naphthyridine.

60. The compound as defined in claim 34, where R is aroyl.

61. The compound as defined in claim 60, where R is benzoyl.

62. The compound as defined in claim 61, where m is 1 and X is H, which is 1-benzoyl-1,2,3,4-tetrahydrobenzo[c]-1,5-naphthyridine.

63. The compound as defined in claim 34, where R is arylloweralkanoyl.

64. The compound as defined in claim 63, where R is phenylacetyl.

65. The compound as defined in claim 64, where m is 1 and X is H, which is 1-(phenylacetyl)-1,2,3,4-tetrahydrobenzo[c]-1,5-naphthyridine.

66. The compound as defined in claim 63, where R is 2-fluorophenylacetyl.

67. The compound as defined in claim 66, where m is 1 and X is H, which is 1-[(2-fluorophenyl)acetyl]-1,2,3,4-tetrahydrobenzo[c]-1,5-naphthyridine.

68. The compound as defined in claim 63, where R is 2-chlorophenylacetyl.

69. The compound as defined in claim 67, where m is 1 and X is H, which is 1-[(2-chlorophenyl)acetyl]-1,2,3,4-tetrahydrobenzo[c]-1,5-naphthyridine.

70. The compound as defined in claim 63, where R is 4-chlorophenylacetyl.

71. The compound as defined in claim 70, where m is 1 and X is H, which is 1-[(4-chlorophenyl)acetyl]-1,2,3,4-tetrahydrobenzo[c]-1,5-napthyridine.

72. The compound as defined in claim 63, where R is 2-methoxyphenylacetyl.

73. The compound as defined in claim 72, where m is 1 and X is H, which is 1-[(2-methoxyphenyl)acetyl]-1,2,3,4-tetrahydrobenzo[c]-1,5-naphthyridine.

74. The compound as defined in claim 63, where R is 4-methoxyphenylacetyl.

75. The compound as defined in claim 74, where m is 1 and X is H, which is 1-[(4-methoxyphenyl)acetyl]-1,2,3,4-tetrahydrobenzo[c]-1,5-naphthyridine.

76. The compound as defined in claim 34, where R is thienylloweralkanoyl.

77. The compound as defined in claim 76, where R is 2-thienylacetyl.

78. The compound as defined in claim 77, where m is 1 and X is H, which is 1-(2-thienyl)acetyl-1,2,3,4-tetrahydrobenzo[c]-1,5-naphthyridine.

79. The compound as defined in claim 76, where R is 3-thienylacetyl.

80. The compound as defined in claim 80, where m is 1 and X is H, which is 1-(3-thienyl)acetyl-1,2,3,4-tetrahydrobenzo[c]-1,5-naphthyridine.

81. The compound as defined in claim 34, where R is loweralkyl.

82. The compound as defined in claim 81, where R is methyl.

83. The compound as defined in claim 82, where m is 1 and X is H, which is 1-methyl-1,2,3,4-tetrahydrobenzo[c]-1,5-naphthyridine.

84. The compound as defined in claim 34, where R is arylloweralkyl.

85. The compound as defined in claim 84, where R is phenylethyl.

86. The compound as defined in claim 85, where m is 1 and X is H, which is 1-(2-phenylethyl)-1,2,3,4-tetrahydrobenzo[c]-1,5-naphthyridine.

87. The compound as defined in claim 84, where R is 3-phenylpropyl.

88. The compound as defined in claim 87, where m is 1 and X is H, which is 1-[3-(phenyl)propyl]-1,2,3,4-tetrahydrobenzo[c]-1,5-naphthyridine.

89. The compound as defined in claim 84, where R is 2-(2-fluorophenyl)ethyl.

90. The compound as defined in claim 89, where m is 1 and X is H, which is 1-[2-(2-fluorophenyl)ethyl]-1,2,3,4-tetrahydrobenzo[c]-1,5-naphthyridine.

91. The compound as defined in claim 84, where R is 2-(2-chlorophenyl)ethyl.

92. The compound as defined in claim 91, where m is 1 and X is H, which is 1-[2-(2-chlorophenyl)ethyl]-1,2,3,4-tetrahydrobenzo[c]-1,5-naphthyridine.

93. The compound as defined in claim 84, where R is 2-(4-chlorophenyl)ethyl.

94. The compound as defined in claim 93, where m is 1 and X is H, which is 1-[2-(4-chlorophenyl)ethyl]-1,2,3,4-tetrahydrobenzo[c]-1,5-naphthyridine.

95. The compound as defined in claim 84, where R is 2-(2-methoxyphenyl)ethyl.

96. The compound as defined in claim 95, where m is 1 and X is H, which is 1-[2-(2-methoxyphenyl)ethyl]-1,2,3,4-tetrahydrobenzo[c]-1,5-naphthyridine.

97. The compound as defined in claim 84, where R is 2-(4-methoxyphenyl)ethyl.

98. The compound as defined in claim 97, where m is 1 and X is H, which is 1-[2-(4-methoxyphenyl)ethyl]-1,2,3,4-tetrahydrobenzo[c]-1,5-naphthyridine.

99. The compound as defined in claim 34, where R is thienylloweralkyl.

100. The compound as defined in claim 99, where R is 2-(2-thienyl)ethyl.

101. The compound as defined in claim 100, where m is 1 and X is H, which is 1-[(2-thienyl)ethyl]-1,2,3,4-tetrahydrobenzo[c]-1,5-naphthyridine.

102. The compound as defined in claim 99, where R is 2-(3-thienyl)ethyl.

103. The compound as defined in claim 102, where m is 1 and X is H, which is 1-[(3-thienyl)ethyl]-1,2,3,4-tetrahydrobenzo[c]-1,5-naphthyridine.

104. A pharmaceutical composition for the treatment of various memory dysfunctions characterized by decreased cholinergic function which comprises an effective amount of a compound as defined in claim 1 and a suitable carrier therefor.

105. A method of treating a patient suffering from a memory dysfunction characterized by decreased cholinergic function which comprises administering to the patient an effective amount of a compound as defined in claim 1.

* * * * *